United States Patent
Satoi et al.

(10) Patent No.: US 10,602,971 B2
(45) Date of Patent: Mar. 31, 2020

(54) BIOLOGICAL INFORMATION DETECTION DEVICE INCLUDING CALCULATION CIRCUIT THAT GENERATES SIGNAL OF BIOLOGICAL INFORMATION

(71) Applicant: Panasonic Intellectual Property Management Co., Ltd., Osaka (JP)

(72) Inventors: Naomi Satoi, Osaka (JP); Teruhiro Shiono, Osaka (JP); Toshiya Fujii, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 536 days.

(21) Appl. No.: 15/417,309

(22) Filed: Jan. 27, 2017

(65) Prior Publication Data
US 2017/0231544 A1   Aug. 17, 2017

(30) Foreign Application Priority Data

Feb. 17, 2016  (JP) .................................. 2016-028038
Oct. 24, 2016  (JP) .................................. 2016-207993

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0077* (2013.01); *A61B 5/0261* (2013.01);
(Continued)

(58) Field of Classification Search
USPC .............................................. 600/300–301
See application file for complete search history.

(56) References Cited

U.S. PATENT DOCUMENTS

2014/0073917 A1* 3/2014 Huang ................ A61B 5/0066
                                                                   600/427
2015/0148687 A1  5/2015 Kitajima et al.
2015/0173618 A1  6/2015 Kusukame

FOREIGN PATENT DOCUMENTS

JP   9-019408     1/1997
JP   2002-071825  3/2002
(Continued)

OTHER PUBLICATIONS

Guillaume Lopez et al., "Continuous blood pressure monitoring in daily life", Journal of Advanced Mechanical Design, Systems, and Manufacturing 4(1), 179-186, Feb. 26, 2010.

*Primary Examiner* — Carl H Layno
*Assistant Examiner* — Dacheng Xie
(74) *Attorney, Agent, or Firm* — McDermott Will & Emery LLP

(57) ABSTRACT

A biological information detection device according to an aspect of the present disclosure includes: a light source that, in operation, emits irradiation light for irradiating a test portion of a subject; a light detector that, in operation, detects light reached from the test portion and that outputs an electrical signal corresponding to the light; and a calculation circuit that, in operation, generates a signal of biological information related to a blood flow in a target area in the test portion based on the electrical signal. The light detector is an image sensor. The electrical signal includes an image signal obtained by the image sensor. The calculation circuit, in operation, detects a magnitude of an inclination of an orientation of the test portion with respect to a reference orientation by image recognition based on the image signal, and determines the target area according to the magnitude of the inclination of the orientation of the test portion.

20 Claims, 19 Drawing Sheets

(51) Int. Cl.
*A61B 5/024* (2006.01)
*A61B 5/107* (2006.01)
*A61B 5/021* (2006.01)
*A61B 5/026* (2006.01)
*A61B 5/1455* (2006.01)
*A61B 5/18* (2006.01)
*G05B 15/02* (2006.01)

(52) U.S. Cl.
CPC ...... *A61B 5/02108* (2013.01); *A61B 5/02416* (2013.01); *A61B 5/1071* (2013.01); *A61B 5/14553* (2013.01); *A61B 5/18* (2013.01); *A61B 5/7275* (2013.01); *G05B 15/02* (2013.01)

(56) References Cited

FOREIGN PATENT DOCUMENTS

| | | |
|---|---|---|
| JP | 2012-057962 | 3/2012 |
| JP | 2012-125370 | 7/2012 |
| JP | 2014-036801 | 2/2014 |
| JP | 2015-100432 | 6/2015 |
| JP | 2015-134157 | 7/2015 |

\* cited by examiner

BIOLOGICAL INFORMATION DETECTION DEVICE INCLUDING CALCULATION CIRCUIT THAT GENERATES SIGNAL OF BIOLOGICAL INFORMATION

BACKGROUND

1. Technical Field

The present disclosure relates to a technique that detects biological information.

2. Description of the Related Art

As basic parameters for determining the physical condition of a human, a heart rate, a blood flow rate, a blood pressure, an oxygen saturation in blood and others are widely used. These pieces of biological information on blood are usually measured by a contact measuring instrument. Since the body of a subject is restrained by a contact measuring instrument, when measurement is continuously made particularly for a long time, discomfort of the subject is caused.

These days, due to increase of chronic disease and aging of the society, practice and diffusion of health care at home are being promoted. Because measurement of biological information conducted in medical facilities has the purpose of curing disease, a patient can bear the pain associated with the measurement. However, for the application of health care at home, diffusion of health care would be difficult if the measurement causes pain or inconvenience. A different approach not the extension of the measurement technique conducted in medical facilities is called for the measurement technique in home medical care. For instance, it is expected that measurement be made naturally in a noninvasive manner, in an unrestrained and non-contact manner, and further in an unconscious state.

Japanese Unexamined Patent Application Publication (JP-A) No. 2002-71825 discloses an example of a method of measuring biological information in a non-contact manner. The human body sensor disclosed in JP-A No. 2002-71825 measures a heart rate, a breathing rate, a body motion using microwave which is invisible to human eyes. In addition, Japanese Unexamined Patent Application Publication Nos. 2014-36801 and 2015-100432 disclose a method of measuring a pulse rate and a breathing rate based on a minute change in brightness not perceivable by human eyes, using a normal camera. Each of the measurement methods observes reflection of electromagnetic waves from a body surface to enable non-contact biological information measurement.

On the other hand, as a method of obtaining biological information on a deeper portion in a noninvasive manner, near infrared spectroscopy (hereinafter, referred to as NIRS) is known. This measurement method uses electromagnetic waves (hereinafter referred to as "light") of near-infrared wavelength range (mainly 700 nm to 1000 nm). The light in the above-mentioned wavelength range has a relatively high transmittance through a body tissue such as muscle, fat and bones, and thus called "biological window". In addition, the light in the above-mentioned wavelength range has the property of being likely to be absorbed by oxyhemoglobin ($HbO_2$) and deoxyhemoglobin (Hb) in blood, and thus NIRS makes it possible to measure changes in a blood flow. NIRS is mainly used for measuring a brain function, and is applied to diagnosis of psychiatric disorders such as depression. An optical brain function measuring device to measure a brain function using NIRS irradiates a subject with near-infrared rays (also referred to as "near-infrared light") from a light source disposed above the scalp of the subject, and detects the light which has passed through the inside of the cerebral cortex by a detector. The oxyhemoglobin concentration and deoxyhemoglobin concentration in the blood flowing through the brain can be calculated based on the signal detected by the detector. The activity state (hereinafter may be called "brain function") of a brain can be estimated based on an oxygenation state of hemoglobin. Japanese Unexamined Patent Application Publication No. 2015-134157 discloses an example of an optical brain function measuring device that measures a brain function utilizing the NIRS.

Japanese Unexamined Patent Application Publication No. 9-19408 discloses a measurement device in which a plurality of light irradiation units and light receiving units are regularly disposed, and a spatial distribution of signals to be measured is calculated from signals detected by the light receiving units.

SUMMARY

In one general aspect, the techniques disclosed here feature a biological information detection device including: a light source that, in operation, emits irradiation light for irradiating a test portion of a subject; a light detector that, in operation, detects light reached from the test portion and outputs an electrical signal corresponding to the light; and a calculation circuit that, in operation, generates a signal of biological information related to a blood flow in a target area in the test portion based on the electrical signal. The light detector is an image sensor. The electrical signal includes an image signal obtained by the image sensor. The calculation circuit, in operation, detects a magnitude of an inclination of an orientation of the test portion with respect to a reference orientation by image recognition based on the image signal, and determines the target area according to the magnitude of the inclination of the orientation of the test portion.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
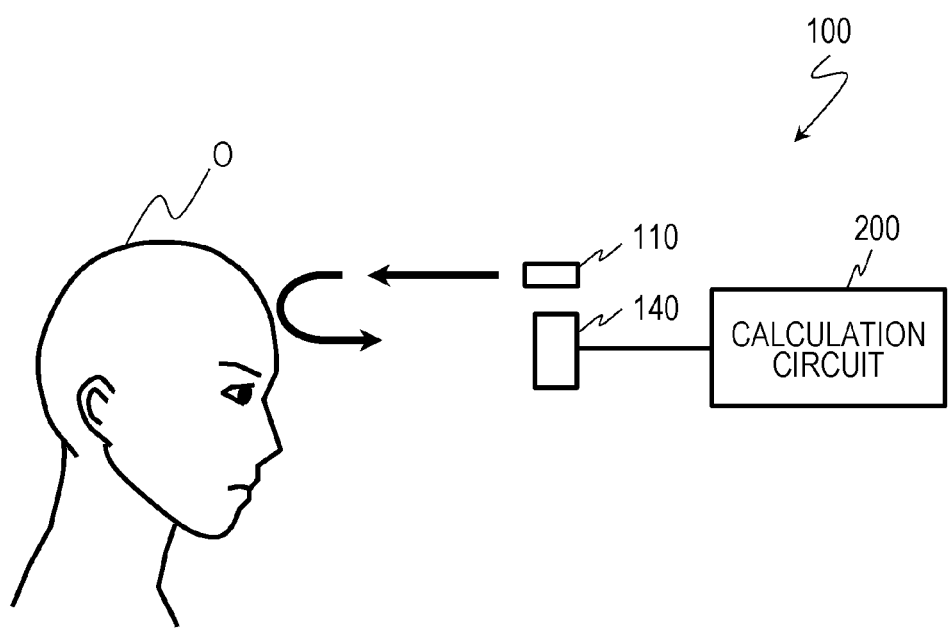
FIG. 1A is a diagram schematically illustrating a general configuration of a biological information detection device in a first embodiment.

The underlying knowledge forming the basis of the present disclosure will be described before descriptions of embodiments of the present disclosure are given.

The inventors study a method of detecting biological information on the blood (for instance, information on a cerebral blood flow) of a subject, and utilizing the biological information for various applications. For instance, the inventors study a method of estimating a level of concentration, emotions and others of a subject, and controlling various instruments according to a result of the estimation. As an example of such control, in application for education using a tablet computer, control that changes contents of display according to a level of concentration of a learner may be adopted. Alternatively, in communication (hereinafter may be referred to as "conversation") of a user with an interactive robot via voice or image, control that changes the contents of the conversation according to a level of concentration or a mental state of the user may also be adopted. In addition, control on an automated driving vehicle according to a level of concentration of a driver, and control on setting the temperature of an air conditioner or changing the sound volume of audio equipment according to an emotion (including sensation of heat, cold, etc.) of an indoor user may also be adopted.

In order to achieve such interactive operations, it is called for that biological information such as a cerebral blood flow of a user (which is also referred to as a "subject" in the present description) be accurately obtained. However, the subject is not still all the time, and usually often moves. The relative position of the subject with respect to a detector changes all the time due to not only a large movement such as walking but also a small body movement caused by a physiological phenomenon. Thus, the signal intensity obtained by a detector varies all the time during measurement. In particular, when a weak signal in a deep portion of a body is detected, it is difficult to observe a temporal variation accurately.

Based on the discussion above, the inventors of the present disclosure have devised a novel biological information measuring technique disclosed below.

The present disclosure includes the biological information detection device described in the following items.

[Item 1]

A biological information detection device according to Item 1 of the present disclosure includes a light source that, in operation, emits irradiation light for irradiating a test portion of a subject, a light detector that, in operation, detects light reached from the test portion and outputs an electrical signal corresponding to the light, and a calculation circuit that, in operation, generates a signal of biological information related to a blood flow in a target area in the test portion based on the electrical signal, in which the light detector is an image sensor, the electrical signal includes an image signal obtained by the image sensor, and the calculation circuit, in operation, detects a magnitude of an inclination of an orientation of the test portion with respect to a reference orientation by image recognition based on the image signal, and determines the target area according to the magnitude of the inclination of the orientation of the test portion.

[Item 2]

In the biological information detection device according to Item 1 of the present disclosure, the calculation circuit may, in operation, determine at least one selected from the group consisting of a shape of the target area, and a position of the target area in the test portion.

[Item 3]

In the biological information detection device according to Item 1 of the present disclosure, the calculation circuit may, in operation, further determine whether or not the magnitude of the inclination of the orientation of the test portion has changed, and when it is determined that the magnitude of the inclination of the orientation of the test portion has changed, the calculation circuit may change a shape of the target area according to the magnitude of the inclination of the orientation of the test portion after the change.

[Item 4]

In the biological information detection device according to Item 1 of the present disclosure, the calculation circuit may, in operation, further determine whether or not the magnitude of the inclination of the orientation of the test portion has changed, and when it is determined that the magnitude of the inclination of the orientation of the test portion has changed, the calculation circuit may change a position of the target area in the test portion according to the magnitude of the inclination of the orientation of the test portion after the change.

[Item 5]

In the biological information detection device according to Item 1 of the present disclosure, the subject includes feature points, and the calculation circuit may, in operation, extract the feature points from the image signal, and detect the magnitude of the inclination of the orientation of the test portion based on positions of the feature points in the image signal.

[Item 6]

In the biological information detection device according to Item 5 of the present disclosure, the calculation circuit may, in operation, predict a propagation path of the light inside the test portion based on the magnitude of the inclination of the orientation of the test portion, and determine the target area based on the predicted propagation path.

[Item 7]

In the biological information detection device according to Item 6 of the present disclosure, the calculation circuit may, in operation, predict an intensity of the light emitted from the test portion or a rate of change of the intensity of the light with respect to a reference value based on at least one selected from the group consisting of the magnitude of the inclination of the orientation of the test portion and the predicted propagation path, and when the predicted intensity of the light or the predicted rate of change of the intensity of the light is smaller than a first value, increase an intensity of the signal of the biological information.

[Item 8]

In the biological information detection device according to Item 7 of the present disclosure, when the predicted intensity of the light or the predicted rate of change of the intensity of the light is larger than a second value, the calculation circuit may decrease the intensity of the signal of the biological information.

[Item 9]

In the biological information detection device according to any one of Items 1 to 8 of the present disclosure, the light detector may, in operation, output the electrical signal at a plurality of times, and the calculation circuit may, in operation, generate the signal of the biological information over time based on the electrical signal outputted from the light detector at the plurality of times.

[Item 10]

In the biological information detection device according to Item 1 of the present disclosure, the calculation circuit may, in operation, further detect a distance between the test portion and the light detector based on the electrical signal, and when the distance is longer than a predetermined distance, the calculation circuit may increase an intensity of the signal of the biological information.

[Item 11]

In the biological information detection device according to Item 10 of the present disclosure, when the distance is shorter than the predetermined distance, the calculation circuit may decrease the intensity of the signal of the biological information.

[Item 12]

In the biological information detection device according to Item 10 of the present disclosure, the calculation circuit may, in operation, further determine whether or not the distance has changed, and when it is determined that the distance has changed, the calculation circuit may change the intensity of the signal of the biological information to a value which is larger as the distance after the change is larger.

[Item 13]

In the biological information detection device according to Item 10 of the present disclosure, for each of one or more pixels contained in the image signal which is in the image signal obtained by the image sensor and which corresponds to the test portion, the calculation circuit may, in operation, detect the distance, generate the signal of the biological information, and adjust the intensity of the signal of the biological information.

[Item 14]

In the biological information detection device according to any one of Items 10 to 13 of the present disclosure, the predetermined distance may be the distance detected by the calculation circuit at a certain time.

[Item 15]

In the biological information detection device according to any one of Items 10 to 13 of the present disclosure, the predetermined distance may be the distance detected by the calculation circuit when the generation of the signal of the biological information is started.

[Item 16]

In the biological information detection device according to any one of Items 10 to 15 of the present disclosure, the irradiation light may be pulsed light, and the calculation circuit may, in operation, detect the distance based on a time from when the light source emits the pulsed light to when the light detector detects the pulsed light.

[Item 17]

The biological information detection device according to any one of Items 10 to 15 of the present disclosure may further include a range sensor that detects a distance to the test portion, in which the calculation circuit may, in operation, adjust the intensity of the signal of the biological information based on the distance detected by the range sensor.

[Item 18]

In the biological information detection device according to any one of Items 1 to 17 of the present disclosure, the light may contain a component with a wavelength of 650 nm or greater and 950 nm or less.

[Item 19]

In the biological information detection device according to any one of Items 1 to 18 of the present disclosure, the test portion may be a forehead of the subject, and the biological information may be information related to a blood flow in the cerebral cortex of the subject.

[Item 20]

The biological information detection device according to Item 20 of the present disclosure includes a calculation circuit that, in operation, generates a signal of biological information related to a blood flow in a target area in a test portion of a subject based on an image signal received from a device including a light source that, in operation, emits irradiation light for irradiating the test portion, and an image sensor that, in operation, detects light reached from the test portion and outputs the image signal of the test portion, in which the calculation circuit, in operation, detects a magnitude of an inclination of an orientation of the test portion with respect to a reference orientation by image recognition based on the image signal, and determines the target area according to the magnitude of the inclination of the orientation of the test portion.

[Item 21]

A control method according to Item 21 of the present disclosure provides a method of controlling a biological information detection device which is used by electrically connecting to a device including a light source that, in operation, emits irradiation light for irradiating a test portion of a subject, and an image sensor that, in operation, detects light reached from the test portion and outputs an image signal of the test portion, the method causing the biological information detection device to: generate biological information related to a blood flow in the test portion based on the image signal outputted from the image sensor; detect a magnitude of an inclination of an orientation of the test portion with respect to a reference orientation by image recognition based on the image signal, and determine a target area in the test portion according to the magnitude of the inclination of the orientation of the test portion, the target area for which the biological information is generated.

[Item 22]

The program according to Item 22 of the present disclosure provides a program to be executed by a computer of a biological information detection device which is used by electrically connecting to a device including a light source that, in operation, emits irradiation light for irradiating a test portion of a subject, and an image sensor that, in operation, detects light reached from the test portion and outputs an image signal of the test portion, the program causing the computer to: generate biological information related to the blood flow in the test portion based on the image signal outputted from the image sensor; detect a magnitude of an inclination of an orientation of the test portion with respect to a reference orientation by image recognition based on the image signal; and determine a target area in the test portion according to the magnitude of the inclination of the orientation of the test portion, the target area for which the biological information is generated.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or a large scale integration (LSI). The LSI or IC can be integrated into one chip, or also can be a combination of plural chips. For example, functional blocks other than a memory may be integrated into one chip. The name used here is LSI or IC, but it may also be called system LSI, very large scale integration (VLSI), or ultra large scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk and a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

Hereinafter, an embodiment of the present disclosure will be described in detail with reference to the drawings. It should be noted that each of the embodiments described below provides a general or specific example. Numerical values, shapes, materials, structural components, the arrangement and connection of the structural components, steps, the sequence of the steps presented in the following embodiments are mere examples, and are not intended to limit the scope of the present disclosure. Various aspects described in the present description may be combined with each other as long as no contradiction occurs. Also, among the structural components in the subsequent embodiment, components not recited in any one of the independent claims which indicate the broadest concepts are described as arbitrary structural components. In the following description, structural components having substantially the same function or similar functions are labeled with a reference symbol in common, and a description may be omitted.

First Embodiment

First, a biological information detection device in a first embodiment of the present disclosure will be described. A biological information detection device 100 in this embodiment measures a cerebral blood flow of a test portion of a subject in a non-contact manner.

FIG. 1A is a diagram schematically illustrating a general configuration of the biological information detection device 100 in the first embodiment.

The biological information detection device 100 includes a light source 110, a light detector 140, and a calculation circuit 200 electrically connected to the light detector 140. The light emitted from the light source 110 is reflected by a test portion (the forehead in this example) of a subject O, and enters the light detector 140. The light detector 140 converts the entered light into an electrical signal, and outputs the signal. The calculation circuit 200 generates biological information related to the blood flow in the test portion based on the signal outputted from the light detector 140.

In the present description, "biological information" indicates various information on blood, such as a heart rate, a blood flow rate, a blood pressure and an oxygen saturation in blood. In particular, in this embodiment, the aforementioned information on the cerebral blood flow is measured by the calculation circuit 200. With this, a level of concentration and a state of feelings of the subject O can be estimated.

To put it simply, the calculation circuit 200 in this embodiment performs the following operations.

(1) When the distance between the light detector 140 and the test portion is longer than a predetermined distance, the signal intensity of biological information is increased and outputted.

(2) When the distance between the light detector 140 and the test portion is shorter than the predetermined distance, the signal intensity of biological information is decreased and outputted.

More specifically, when the distance between the light detector 140 and the test portion changes, the calculation circuit 200 changes the signal intensity of biological information to a larger value for the longer distance, and outputs the value. The "predetermined distance" may be a preset distance used as a reference for comparison, or a detected distance between the test portion and the light detector 140 at a certain time. For instance, the distance between the light detector 140 and the test portion when detection of biological information is started may be the "predetermined distance".

As a result, even when the distance changes, information recognized by a user hardly changes. A large change in a signal due to a distance change is reduced, and weak change in biological information is continuously observed (without being significantly varied due to a change in the distance). This allows intuitive comparison between biological states in the past and the current.

When the state of the blood flow of the subject O remains the same, the above-mentioned operation makes it possible to obtain biological information at substantially the same signal level regardless of the position and orientation of a test portion. Thus, for instance, biological information is obtained over time, and comparison of the temporal change in the biological information is made easy.

Hereinafter, the configuration and operation of this embodiment will be described in detail.

[1-1. Configuration of Biological Information Detection Device 100]

Figure 1B:
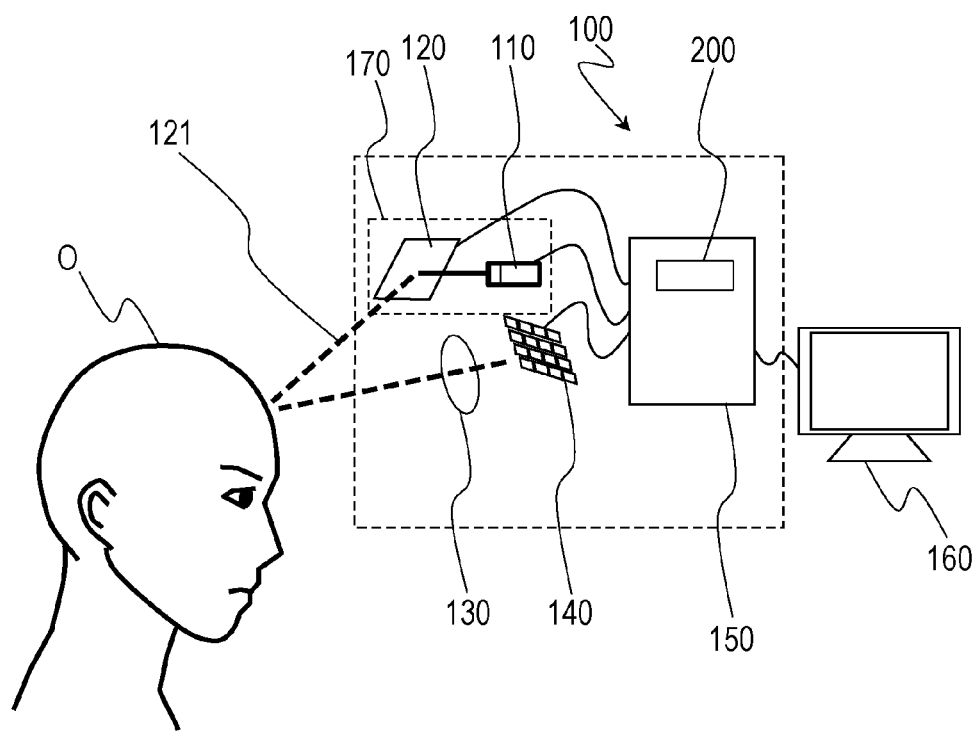
FIG. 1B is a diagram illustrating a more detailed configuration example of the biological information detection device in the first embodiment.

FIG. 1B is a diagram illustrating a more detailed configuration example of the biological information detection device 100 in this embodiment. In addition to the above-described light source 110, light detector 140, calculation circuit 200, the biological information detection device 100 in the example includes an optical element 120 that changes the path of the light emitted from the light source 110, an optical system 130 that collects the light from the subject O, and a processor 150 that processes a signal outputted from the light detector 140, and controls the light source 110, and the optical element 120. The calculation circuit 200 is provided inside the processor 150. FIG. 1B also illustrates a display device (display) 160 which is an external component of the biological information detection device 100. The display device 160 is connected to the processor 150, and displays a processing result.

The light source 110 and the light detector 140 may be integral with or may not be integral with the calculation circuit 200 and the display device 160. Wireless communication may be performed between the light detector 140, the calculation circuit 200, and the display device 160. The biological information detection device 100 may include a communication circuit that transmits and receives information. The calculation circuit 200 may be installed in a computer (for instance, a server computer) disposed at a position distant from the biological information detection device 100. The biological information detection device 100 may transmit an output signal from the light detector 140 to the calculation circuit 200 in a remote place via a network such as the Internet, and may cause the calculation circuit 200 to generate and analyze biological information.

Hereinafter, the details of each component will be described.

The light source 110 irradiates a test portion of the subject O with light. The test portion in this embodiment is the forehead of the subject O. The information on the cerebral blood flow can be obtained by irradiating the forehead with light and detecting scattered light. In the present description, the "scattered light" includes reflected scattered light and transmitted scattered light. In the following description, reflected scattered light may be simply referred to as "reflected light". When biological sensing is performed for information other than the cerebral blood flow, not only reflected scattered light but also transmitted scattered light may be utilized. When information on blood other than the cerebral blood flow is obtained, a part other than the forehead (for instance, an arm or a leg) may be a test portion. In the following description, the test portion is the forehead unless otherwise stated particularly. The subject O is assumed to be a human. However, the subject O may be other than a human, specifically an animal having a skin with part in which no hair is grown. The term "subject" in the present description indicates a general subject including such an animal.

The light source 110 emits light with a wavelength of 650 nm or greater and 950 nm or less, for instance. This wavelength range is included in a wavelength range from red to the near-infrared. The aforementioned wavelength range is called "biological window," and it is known that the absorptivity of the light in the wavelength range within the body is low. Although the light source 110 in this embodiment will be described as a component that emits light in the aforementioned wavelength range, light in another wavelength range (for instance, near-ultraviolet) may be used. In the present description, the term "light" is used for not only visible light but also infrared rays and ultraviolet rays. It is to be noted that with the technique of the present disclosure, electromagnetic waves with a wavelength other than the wavelength of visible light, infrared rays, and ultraviolet rays, for instance, microwave can be utilized as a probe.

Figure 2:
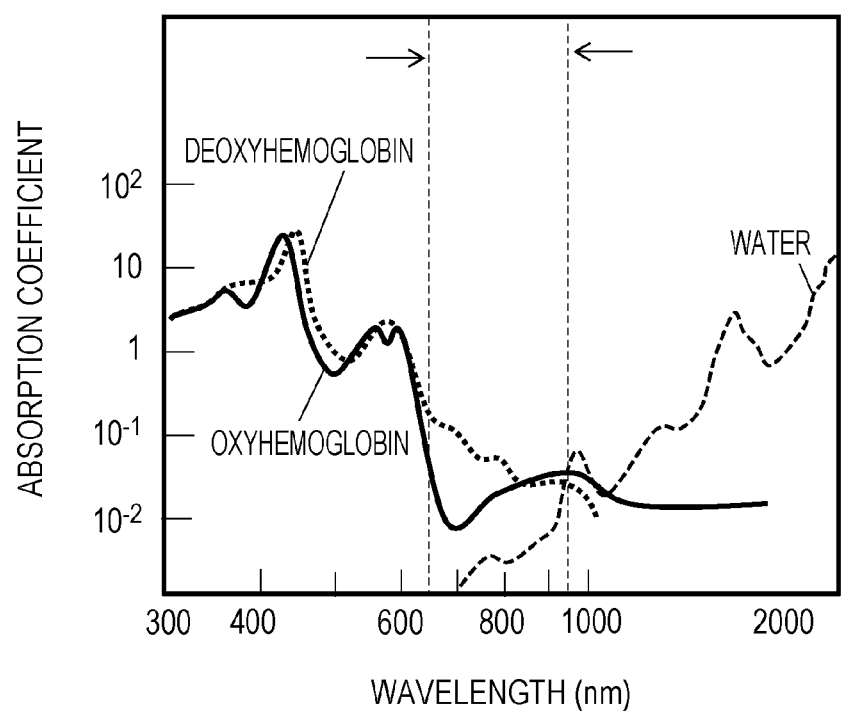
FIG. 2 is a graph illustrating a wavelength dependence of light absorption coefficient of each of oxyhemoglobin, deoxyhemoglobin, and water.

FIG. 2 is a graph illustrating a wavelength dependence of light absorption coefficient of each of oxyhemoglobin, deoxyhemoglobin, and water. In the visible light range with 650 nm or less, light absorption by the hemoglobin ($HbO_2$ and Hb) in blood is high, whereas in the wavelength range with 950 nm or greater, light absorption by water is high. On the other hand, in the wavelength range of 650 nm or greater and 950 nm or less, the absorption coefficients of hemoglobin and water are relatively low, and the scattering coefficients are relatively high. Thus, light in the wavelength range, after entering the inside of a body, is severely scattered and returned to the body surface. Consequently, information on the inside of a body can be efficiently obtained. Thus, in this embodiment, the light in the aforementioned wavelength range is mainly used.

The light source 110 may be a laser light source such as a laser diode (LD) that continuously emits pulsed light, for instance. When the subject O is a human as in this embodiment, the effect of emitted light on the retina is usually taken into consideration. When a laser light source is used as the light source 110, a laser light source may be used that satisfies laser safety standard Class 1 which is formulated in each country. When Class 1 is satisfied, the subject O is irradiated with low illumination light with accessible emission limit, AEL less than 1 mW. However, the light source 110 itself may not satisfy Class 1. For instance, the laser safety standard Class 1 may be satisfied by diffusing or attenuating light using an element such as a diffuser plate and an ND filter disposed between the light source 110 and the subject O.

The light source 110 is not limited to a laser light source and may be another type of light source such as a light emitting diode (LED). As the light source 110, for instance, a semiconductor laser, a solid-state laser, a fiber laser, a superluminescent diode, or an LED may be widely used. The entire device can be miniaturized by combining one of these and a small-sized optical element 120. The light source 110 is not limited to a light source that emits pulsed light, and may be a light source that emits continuous light.

The light source 110 starts or stops light-emission, and changes the power of light-emission according to a command from the processor 150. Light 121 emitted from the light source 110 is used to detect information on cerebral blood flow, and the position of and distance to the forehead.

The optical element 120 is disposed on an optical path of the light 121, between the light source 110 and a test portion (the forehead) of the subject O. The optical element 120 changes the optical path of the light 121 to guide the optical path to the forehead. In response to a command from the processor 150, the optical element 120 adjusts the irradiation position of the light 121 on the forehead. When the optical element 120 includes a mirror, the irradiation position of the light 121 on the forehead is changeable by changing the angle of the mirror.

The optical element 120 may be, for instance, a micro electro mechanical system (MEMS) mirror. Use of particularly a dual-axis scanning mirror enables two dimensional adjustment of the irradiation position of light at a test portion. This enables compact and quick adjustment of an irradiation position of light. In addition, as the optical element 120, for instance, a polygon mirror, a galvano mirror, or a rotational prism may be used.

In the present description, the combination of the light source 110 and the optical element 120 may be referred to as the "light source unit". A light source unit 170 including the light source 110 and the optical element 120 may be formed as an optical module, for instance. In the present description, an emission direction of light from the light source unit 170 may be expressed as an "emission direction of light from the light source".

Figure 1C:
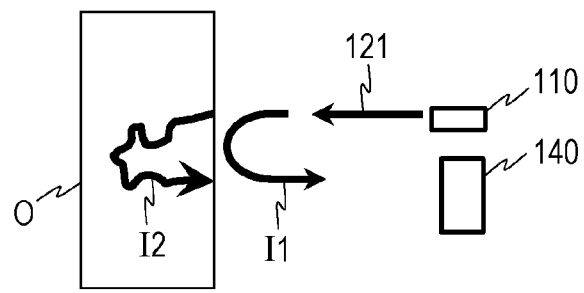
FIG. 1C is a diagram schematically illustrating the manner in which light reflected and scattered by a subject irradiated with light reaches a light detector.

FIG. 1C is a diagram schematically illustrating the manner in which the light (which is referred to as "return light") reflected and scattered by subject O irradiated with the light 121 reaches the light detector 140. The return light from the subject O includes a component reflected by the surface of the subject O (surface reflection component I1), a component (internal scattering component I2) which is reflected once inside the subject O, scattered, or multiply scattered. Between these, a component desired to be detected is the internal scattering component I2. However, in general, the signal intensity of the internal scattering component I2 is low. This is because, as described above, in addition to irradiation with an extremely small quantity of light satisfying the laser safety standard, scattering and absorption of light by the scalp, cerebral fluid, skull bone, gray matter, white matter, and blood flow is high. Furthermore, change in signal intensity, which is caused by a change in blood flow rate or blood flow component when the brain is active, corresponds to one-several tenths of the aforementioned signal intensity, and is extremely small. Thus, detection may be made without allowing the presence of the surface reflection component I1 as much as possible, the surface reflection component I1 being equivalent to several thousand to several ten thousand times a signal component to be detected. Thus, the light detector 140 may be formed of an image sensor having the function of an electronic shutter, and the processor 150 may appropriately control shutter timing, thereby detecting the internal scattering component I2 only. Such a configuration is disclosed, for instance, in the description of Japanese Patent Application No. 2015-122390. The entire disclosure of Japanese Patent Application No. 2015-122390 is incorporated in the present application.

The optical system 130 focuses the light 121 reflected or scattered by a test portion to the light detector 140. The optical system 130 is, for instance, a single or multiple lens, and may include a mirror. When the optical system 130 includes a lens, the light-receiving surface and light-emitting surface of the lens may be each provided with an antireflective coating that reduces reflection of the light 121. This enables detection of information on cerebral blood flow with higher sensitivity.

The light detector 140 detects return light from the subject O. The light detector 140 includes a plurality of light detection elements arranged one-dimensionally or two-dimensionally. Each of the light detection elements includes, for instance, a photodiode, and outputs an electrical signal according to the power (or a light quantity) of the light 121 from a test portion. The light detection element may be another element such as a photomultiplier tube (PMT). Using a highly sensitive avalanche photodiode or photomultiplier tube as a light detection element makes it possible to obtain information on cerebral blood flow with higher sensitivity.

The light detector 140 may be an image sensor (image pickup device) such as a CCD and a CMOS having sensitivity to light in a wavelength range including the wavelength of the light emitted from the light source 110. Using an image sensor makes it possible to obtain a two-dimensional intensity distribution (for instance, moving images) of light. In this case, an electrical signal outputted by the light detector 140 includes an image signal. The calculation circuit 200 utilizes the obtained moving images to extract a characteristic pattern of the test portion by image recognition, and can identify the position of the test portion in the images. Movement of the test portion may be detected by movement detection.

The light detector 140 may have a configuration that allows measurement of the distance to the subject O. The distance to the subject O can be measured using a time-of-flight (TOF) technique, for instance. In the TOF technique, a time taken for irradiation light (for instance, pulsed light) to reach the light detector 140 after reflected by the subject O, in short, a time of flight is measured. The calculation circuit 200 can detect the distance to a test portion based on the time from when the light source 110 emits pulsed light to when the light detector 140 detects the pulsed light. The time-of-flight can be measured based on the difference between the phase of light detected by each detection element and the phase of light in the light source 110. A compound-eye camera may be used as the light detector 140. A compound-eye camera has a plurality of image sensors, and can measure a distance based on the parallax between a plurality of obtained images. Like this, the light detector 140 may be a device that can obtain both image information and distance information.

Information on the distribution of the distance between the subject O and the biological information detection device 100 may be generated by the calculation circuit 200 based on the output of the light detector 140 or generated by the light detector 140 and transmitted to the calculation circuit 200.

The image information and the distance information may be obtained utilizing a plurality of devices such as combining the light detector 140 that obtains image information and a range sensor. In such a configuration, the calculation circuit 200 adjusts the signal intensity of biological information based on the distance detected by the range sensor. A distance may be measured by a method different from the method using the TOF or a compound-eye camera. For instance, the calculation circuit 200 may detect the distance between the light detector 140 and a test portion based on the size of the test portion (forehead), which is identified based on the image signal outputted from the light detector 140. Since the angle of view of each image obtained by the light detector 140 is predetermined, the distance to the test portion can be determined based on the size of the area of the test portion in the image.

It is to be noted that the optical system 130 and the light detector 140 may be integrally formed. In addition, the light source unit 170, the optical system 130, and the light detector 140 may be integrally formed. In this manner, a portable small-sized optical unit is implemented. A small-sized optical unit may be connected to the processor 150 by a cable such as a USB cable.

Figure 3:
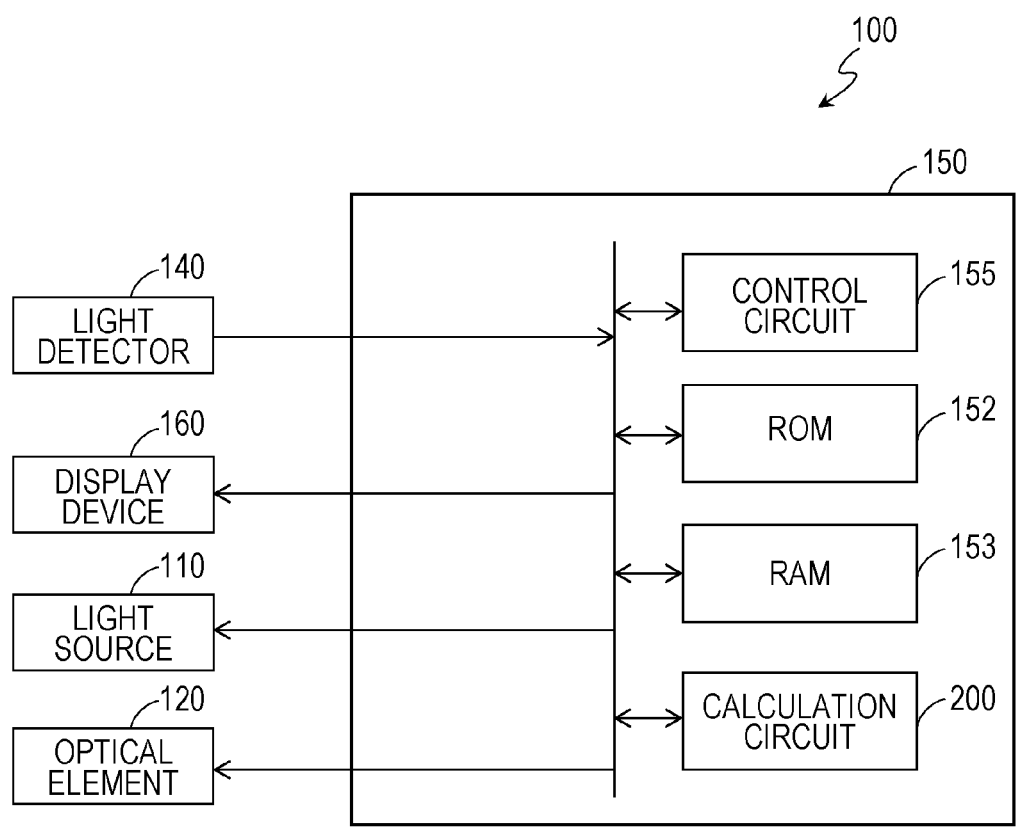
FIG. 3 is a diagram illustrating an internal configuration of a processor.

FIG. 3 is a diagram illustrating the internal configuration of the processor 150.

The processor 150 is connected to the light source 110, the optical element 120, the light detector 140, and the display device (the display) 160, and controls these components. The processor 150 includes a read only memory (ROM) 152, a random access memory (RAM) 153, a control circuit 155, and the calculation circuit 200. The control circuit 155 is an integrated circuit including, for instance, a central processing unit (CPU). The control circuit 155 controls the entire operation of the biological information detection device 100. The calculation circuit 200 is a signal processing circuit such as a digital signal processor (DSP). The calculation circuit 200 may be an integrated circuit such as an application specific integrated circuit (ASIC) and a field-programmable gate array (FPGA).

The calculation circuit 200 generates biological information based on an electrical signal obtained by the light detector 140. In this process, an area (referred to as a "target area" in the present description) which is a target in the image and for which biological information is generated is changed according to the position and posture (inclination angle) of the test portion of the subject O, and the signal intensity of biological information is changed. The calculation circuit 200 detects a distance, generates biological information, and adjusts the signal intensity of the biological information for each of pixels or each of pixel groups in an image area corresponding to the test portion, out of the image signal obtained by the light detector 140 (image sensor). The details of the processing performed by the calculation circuit 200 will be described later.

The ROM 152 stores computer programs to be executed by the control circuit 155 and the calculation circuit 200. Each of the computer programs is a group of commands that cause the control circuit 155 and the calculation circuit 200 to execute, for instance, the processing or part of the processing illustrated by the later-described flowchart. Such a computer program is downloadable, for instance, via a network, and may be stored in a computer-readable recording medium. The RAM 153 is a work memory for loading a program which is to be executed by the control circuit 155 and the calculation circuit 200. The RAM 153 is also a storage device (a storage medium) that stores a signal (data) outputted from the light detector 140 and data on measured biological information.

The processor 150 may be a general-purpose computer such as a personal computer, a tablet computer, and a smartphone. Such a computer includes a CPU that controls the entire operation of the processor 150. The CPU may execute part or all of the operation to be performed by the calculation circuit in the present disclosure. In that case, the CPU of the general-purpose computer functions as at least part of the "calculation circuit" in the present disclosure. When the function of this embodiment is achieved by a computer with a built-in camera, part of the function of the light detector 140 may be achieved by the built-in camera in the computer. For instance, the test portion may be detected by image recognition using a visible light image captured by the camera, and information on the near-infrared light and red light necessary for generation of biological information may be obtained by an external light detector 140. Although a normal camera has an IR-cut filter to obtain a visible light image, the light detector 140 has no IR-cut filter to allow detection of the near-infrared light emitted from the light source 110.

The light source 110, the optical element 120, and the light detector 140 are connectable to the processor 150 via various interfaces. For instance, when the light detector 140 is an image sensor, those components are connectable to the processor 150 utilizing a terminal in accordance with the MIPI Standard®. Also, the light source 110 and the optical element 120 are connectable to the processor 150 utilizing a USB interface, for instance.

As illustrated, the processor 150 connectable to the display device 160 that displays moving images and biological information of a subject. The display device 160 is a liquid crystal or organic EL display, for instance. The display device 160 is connectable to the processor 150 utilizing a terminal in accordance with the HDMI® standard, for instance. A user of the biological information detection device 100 can obtain various information on biological activity from the display device 160.

It is also possible to transmit and/or receive data by wireless communication other than the above-described connection via a cable. It is possible to utilize communication in accordance with the Wi-Fi® standard or the ZigBee® standard, for instance.

The biological information detection device 100 can measure a two-dimensional intensity distribution of light, and to measure various biological information such as a blood flow rate, a blood pressure, an oxygen saturation in blood, and a heart rate in the brain based on the intensity distribution. Such a measurement technique is disclosed by JP-A 2015-134157, and can be preferably utilized in the present disclosure. The entire disclosure of JP-A 2015-134157 is incorporated by reference in the present application.

It is known that there is a close relationship between a change in cerebral blood flow rate or blood flow component (for instance, hemoglobin) and neural activity of human. For instance, in response to a change in feelings of human, the activity of nerve cells changes, and thereby the cerebral blood flow rate or blood flow component is changed. Thus, measurement of biological information such as a change in the cerebral blood flow rate and blood flow component makes it possible to estimate the mental state of a subject. The mental state of a subject indicates, for instance, a feeling (such as comfort and discomfort), an emotion (such as relief, anxiety, sadness and anger), a physical condition (such as liveliness and fatigue), and temperature sensation (such as hot, cold and sultry). In addition, as a derivative state, the mental state also includes an index indicating a degree of brain activity, for instance, a level of proficiency, a level of mastery, and a level of concentration.

[1-2. Operation of Biological Information Detection Device]

Next, the operation of the biological information detection device 100 in this embodiment will be described. In the following description, the light detector 140 is assumed to be an image sensor that outputs an image signal.

The biological information detection device 100, when receiving a command to start detection of biological information from a user, irradiates the subject O with light from the light source 110 and detects light reflected from the subject O by the light detector 140. The detection is performed over time until a command to stop the detection is received, and signals of moving images are outputted from the light detector 140. The calculation circuit 200 generates biological information at a test portion based on the signals of the moving images. In this process, the calculation circuit 200 changes an area (referred to as a "target area" in the present description) which is a target on the image and for which biological information is generated, according to movement of the test portion, and adjusts the signal intensity of biological information generated. The movement of the test portion includes a planar movement with almost no change in the distances from the light detector 140, a movement with a uniform change in the distances of the test portion, and a movement with a partial change in the distances of the test portion. The calculation circuit 200 performs processing according to these three types of movement.

<Planar Movement>

Figure 4A:
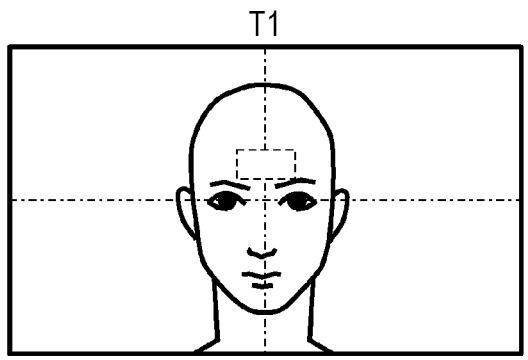
FIG. 4A is an illustration indicating image information obtained by the light detector at a first time.

FIG. 4A illustrates image information obtained by the light detector 140 at time T1. The calculation circuit 200 has a face recognition function, and detects whether a human face is included in the image information outputted from the light detector 140. The calculation circuit 200 determines the forehead area (area within a dashed line frame in FIG. 4A) which is a target area for which biological information is measured, based on the positions of feature points (such as the eyes, nose and mouth) in the face.

Figure 4B:
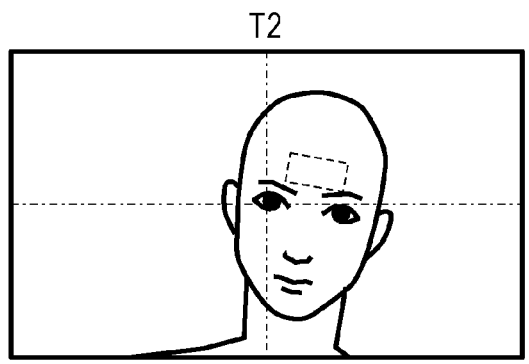
FIG. 4B is an illustration indicating image information obtained by the light detector at a second time.

FIG. 4B illustrates image information obtained by the light detector 140 at time T2. During an interval from time T1 to time T2, the test portion of the subject only moves substantially parallel to an image obtaining surface (image capture surface) of the light detector 140, and only rotates around an axis substantially perpendicular to the image obtaining surface. The distance between the light detector 140 and the test portion has not changed. Thus, the calculation circuit 200 detects a change in the position of the forehead in the obtained image, and changes the position of the forehead area for which biological information is measured.

<Change in Distance>

Figure 4C:
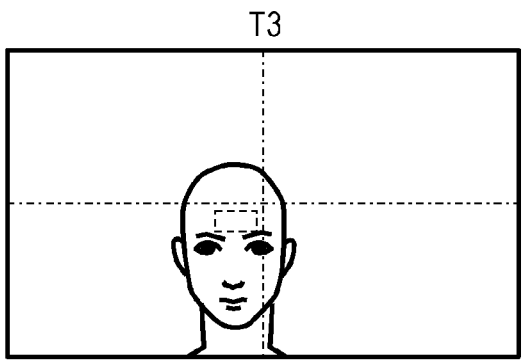
FIG. 4C is an illustration indicating image information obtained by the light detector at a third time.

FIG. 4C illustrates image information obtained by the light detector 140 at time T3. At time T3, compared with time T1, the subject is more away from the light detector 140. At time T3, the calculation circuit 200 detects a change in the positions of feature points in the face, and changes the position and size of a target area for which biological information is measured. The calculation circuit 200 further predicts attenuation of the signal intensity of the biological information due to the change in the distance, and adjusts the signal intensity.

Figure 5A:
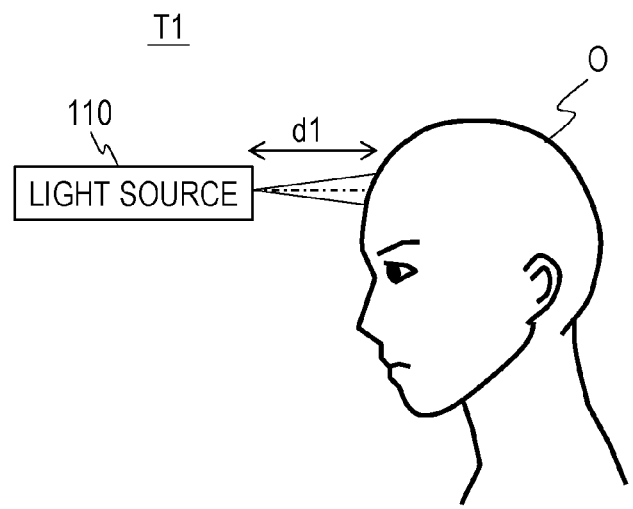
FIG. 5A is a schematic illustration of a positional relationship between a light source and the subject at the first time.
Figure 5B:
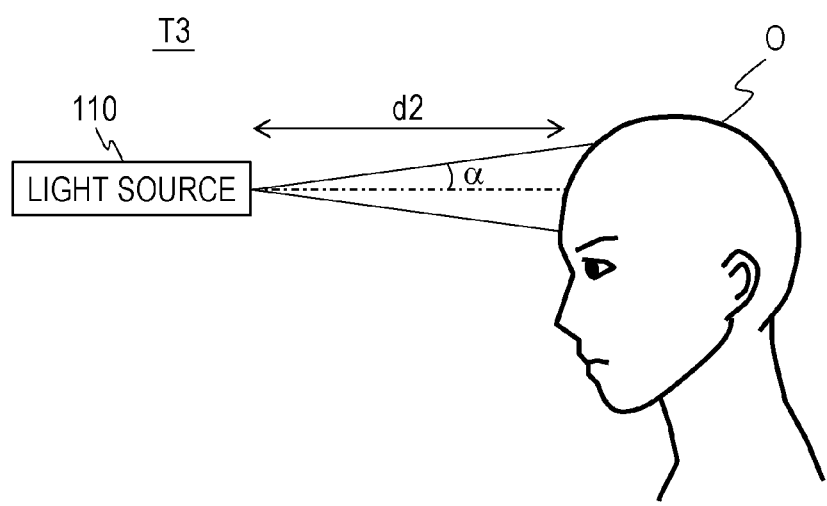
FIG. 5B is a schematic illustration of a positional relationship between the light source and the subject at the third time.

FIGS. 5A and 5B are schematic illustrations of the positional relationship between the light source 110 and the subject O at times T1 and T3, respectively. Here, it is assumed that the light irradiated from the light source 110 is scattered light with a spread angle of α in a uniform distribution, and the distance between the light source 110 and the subject O at times T1 and T3 are d1 and d2, respectively. In this case, the illumination intensity at the forehead at time T3 is $(d1/d2)^2$ times the illumination intensity at time T1. In other words, the density of light emitted to the test portion is decreased as the distance between the light source 110 and the test portion is larger. Accordingly, the signal intensity of biological information is also attenuated. The calculation circuit 200 multiplies the signal intensity of the biological information obtained at time T3 by $(d2/d1)^2$. With this, it is possible to directly compare the biological information obtained at times T1 and T3, respectively. Although when the light from the light source has no uniform distribution, the following does not hold, if the illumination intensity distribution of the light source is known, the calculation circuit 200 is able to calculate an attenuation rate of biological information due to an increase or decrease in the distance between the light source 110 and the test portion, and to adjust the signal intensity. Since noise such as ambient light for measurement increases as the distance between the light detector 140 and the test portion is larger, the SN ratio of detected biological information is also changed. The calculation circuit 200 adjusts the biological information in consideration of an increase or decrease in the signal due to movement of the subject as described above.

<Change in Angle>

Figure 4D:
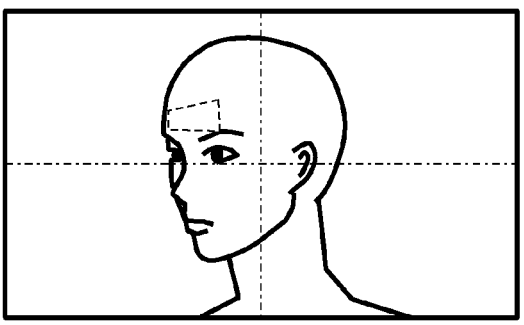
FIG. 4D is an illustration indicating image information obtained by the light detector at a fourth time.

FIG. 4D illustrates image information obtained by the light detector 140 at time T4. At time T4, compared with time T1, the subject O turns around an axis in the vertical direction, and the forehead area as the test portion is inclined with respect to the image obtaining surface. For this reason, in the image signal, the shape of the area corresponding to the forehead area has changed. The calculation circuit 200 detects a change in the shape of the forehead area based on the change in the positions of the plurality of feature points in the face, and modifies the target area for which biological information is measured, according to the change. In this example, the left-side area located in the back of the forehead area in FIG. 4D has a relatively large distance from the light detector 140. Thus, the target area, which is a rectangle at time T1, is deformed to a shape with a narrow vertical width on the left side. In addition, since the distance from the light detector 140 to each point in the target area changes, the calculation circuit 200 adjusts the signal intensity of biological information for each point in the target area. The adjustment may be made for each of pixels or for each of neighboring pixel sets (pixel groups) each including a plurality of pixels. For adjustment of biological information, fine adjustment can be made, when it is possible to obtain information on the illumination intensity distribution data of the light source, the illumination intensity distribution data of ambient light, and the distribution of the distance between the subject O and the biological information detection device 100.

By the processing described above, appropriate biological information can be generated according to the movement of the test portion. Thus, for instance, when biological information is obtained over time, it is possible to reduce the variation in the signal level and to make comparison easy.

Next, an example of the entire operation of the biological information detection device 100 in this embodiment will be described.

Figure 6:
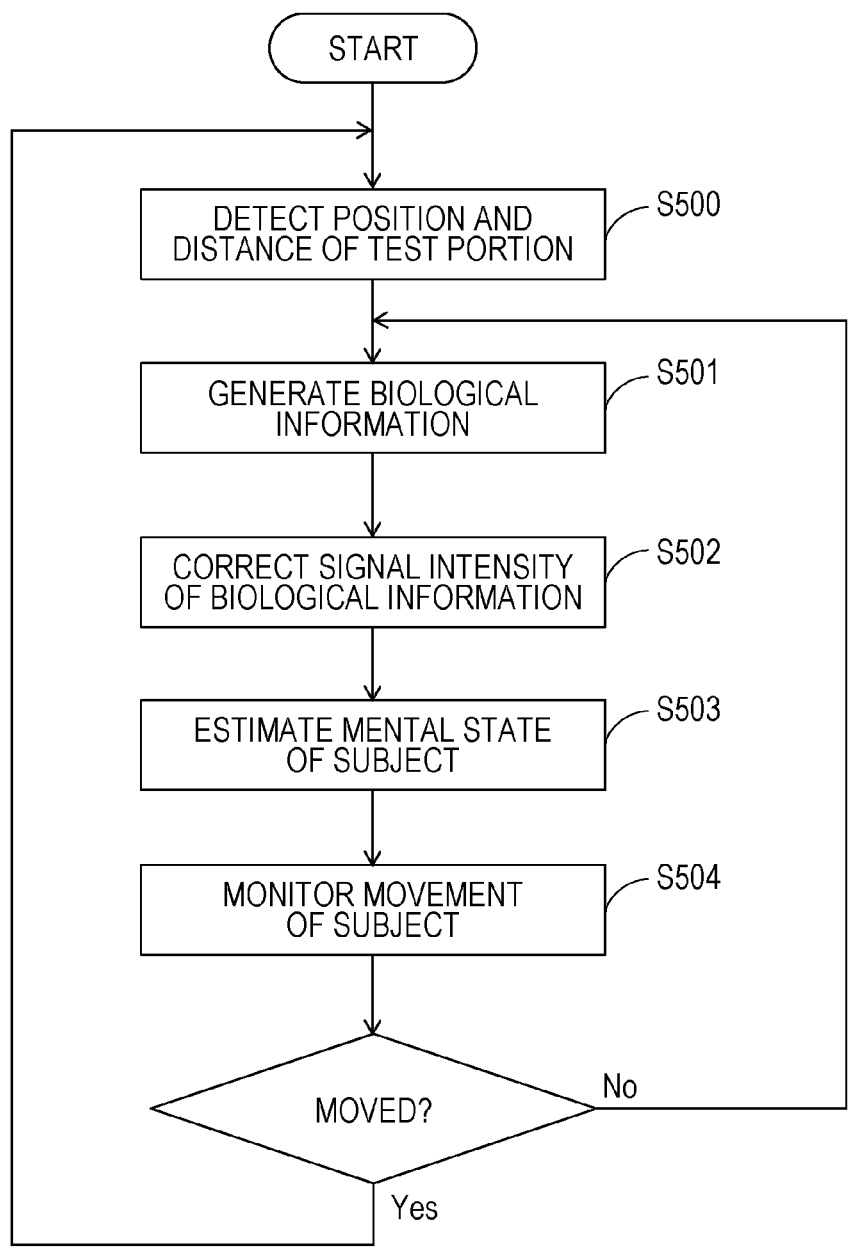
FIG. 6 is a flowchart illustrating an example of an operation of the biological information detection device.

FIG. 6 is a flowchart illustrating an example of the operation of the biological information detection device 100. Hereinafter, a description is given under the assumption that the light detector 140 is a TOF image sensor.

(Step S500)

The calculation circuit 200 detects the position of the test portion (forehead) of the subject O, and the distance between the light detector 140 and the forehead based on the image signal outputted from the light detector 140. Specifically, the calculation circuit 200 identifies whether or not the forehead of the subject O is present in the frame image outputted from the light detector 140, and identifies the position of the forehead by image recognition. The calculation circuit 200 detects the presence of the forehead and identifies the position of the forehead based on the positions of the feature points (such as the eyes, nose and mouth) in the face. In this process, the position of the forehead may be identified by pattern matching using templates associated with the human forehead. The templates are pre-stored in a ROM 152, for instance. For the image recognition, a variety of heretofore known techniques may be used without being limited to a specific technique. The calculation circuit 200 further measures (ranges) the distance to each point of the test portion based on the difference between the phase of the light emitted from the light source 110, and the phase of the light detected by the light detector 140. The calculation circuit 200 performs measurement of the distance for each of pixels in an area corresponding to the test portion in the image, or for each of neighboring pixel groups each including a plurality of pixels.

(Step S501)

The calculation circuit 200 generates biological information on a target area corresponding to the test portion of the subject O in the image based on the image signal outputted from the light detector 140. For instance, as biological information, the calculation circuit 200 generates information indicating the oxyhemoglobin concentration and deoxyhemoglobin concentration in the blood in the brain. The calculation circuit 200 generates the biological information for each of pixels in an area corresponding to the test portion in the image, or for each of neighboring pixel groups.

Here, a specific example of a method for measuring biological information will be described.

A major role of blood is to receive oxygen from the lungs and carry the oxygen to tissues, and to receive carbon dioxide from the tissues to circulate the carbon dioxide in the lungs. Approximately 15 g of hemoglobin is present in 100 ml of blood. Oxyhemoglobin is hemoglobin combined with oxygen, whereas deoxyhemoglobin is hemoglobin not combined with oxygen. As illustrated in FIG. 2, oxyhemoglobin and deoxyhemoglobin have different light absorption properties. Oxyhemoglobin absorbs infrared rays with a wavelength greater than approximately 830 nm relatively well, and deoxyhemoglobin absorbs red light (for instance, a wavelength of 660 nm) relatively well. The rates of absorption of near-infrared rays with a wavelength of 805 nm are the same for both oxyhemoglobin and deoxyhemoglobin. Thus, in this embodiment, two wavelengths of 660 nm (red light) and 830 nm (infrared light) are used, and the light power from a test portion is measured for each of the wavelengths. Based on the powers of these red light and infrared light, the oxygen saturation of the hemoglobin can be determined. As a combination of two wavelengths to be used, a combination of a wavelength shorter than 805 nm and a wavelength longer than 805 nm may be used. The oxygen saturation is a value that indicates the percentage of hemoglobin combined with oxygen out of the hemoglobin in blood. The oxygen saturation is defined by the following expression, where C (Hb) is the concentration of deoxyhemoglobin, and C (HbO$_2$) is the concentration of oxyhemoglobin:

Oxygen saturation=C(HbO$_2$)/[C(HbO$_2$)+C(Hb)]×100 (%).

A human body contains, other than the blood, a component that absorbs light with a wavelength of red to near-infrared rays, and a temporal variation of rate of absorption of light is mainly caused by the hemoglobin in arterial blood. Thus, an oxygen saturation in blood can be measured with high accuracy based on the variation of rate of absorption. The arterial blood pumped from the heart flows through the blood vessels as pulse waves. On the other hand, the venous blood has no pulse wave. Light, with which a living body is irradiated, passes through the living body while being absorbed by tissues in the living body, such as an artery, vein and tissues other than the blood. The thickness of each tissue other than the arteries has no temporal variation. Thus, scattered light from the inside of a living body exhibits a temporal change in intensity according to a change of the thickness of an arterial blood layer due to pulsation. The change in intensity reflects the change of the thickness of the arterial blood layer, and is free from the effect of the venous blood and the tissues. Thus, the information on arterial blood can be obtained by focusing attention on only varied components of the scattered light. A pulse rate can also be determined by measuring the period of a component that changes with time.

(Step S502)

The calculation circuit 200 adjusts the signal intensity of the generated biological information according to the distance to each pixel or each pixel group in an target area. The calculation circuit 200 adjusts the signal intensity to an appropriate level according to the movement of the test portion by the method which has been described with reference to FIGS. 4A to 4D and 5A to 5B. Thus, even when the test portion moves, it is easy to compare between pieces of biological information obtained at different times.

(Step S503)

The calculation circuit 200 estimates a mental state of the subject based on the biological information. For instance, the calculation circuit 200 estimates a mental state such as a level of concentration and an emotion of the subject O based on the oxygenation state of hemoglobin. When nerve cells are active, the oxygen carried by the hemoglobin in the blood in the capillary vessels is consumed. It is known that an increase in blood flow occurs associated with local response due to the consumption of oxygen. Also, it is known that the deoxyhemoglobin temporarily increases because of delivery of oxygen to a body tissue by the oxyhemoglobin in the capillary vessels. For instance, it is assumed that the subject O is learning by solving a problem. In this case, the cerebral blood flow rate may change every moment according to a level of concentration. As the level of concentration enhances, the cerebral blood flow rate increases, and the oxygen saturation in blood tends to decrease. Thus, the calculation circuit 200 can determine the level of concentration of the subject O based on, for instance, the amount of change from a reference value of the cerebral blood flow rate or the oxygen saturation in blood. In this embodiment, a table is pre-stored in the ROM 152, which associates a level of concentration with the amount of change from a reference value of the cerebral blood flow rate or the oxygen saturation in blood. The calculation circuit 200 can determine the level of concentration of learning from the measured biological information by referring to the table. Results of measurement and estimation by the calculation circuit 200 are temporarily saved in a storage medium such as the RAM 153, for instance.

(Step S504)

As described above, it is assumed that the subject O is learning by solving a problem, for instance. In this case, it is presumed that the head of the subject O, specifically, the forehead as a test portion moves during measurement. Thus, the calculation circuit 200 monitors all the time whether or not the subject (particularly, the head) has moved. For instance, the calculation circuit 200 calculates a motion vector between the consecutive frame images. When the magnitude of the motion vector is greater than or equal to a threshold value, the calculation circuit 200 determines that the subject O has moved, and when the magnitude of the motion vector is less than the threshold value, the calculation circuit 200 determines that the subject O has not moved. For instance, the threshold value is pre-stored in the ROM 152.

The calculation circuit 200 does not need to determine the movement of the test portion of the subject O successively, and may determine the movement for every predetermined number of frames (for instance, 300 frames). In this manner, the power consumption of the calculation circuit 200 can be reduced.

When the calculation circuit 200 does not detect movement of the test portion of the subject O, the processing returns to step S501 again. When the calculation circuit 200 detects movement of the test portion of the subject O, the processing returns to step S500.

It is to be noted that the processing may be configured such that without the monitoring using the motion vector, the measurement of biological information in step S502 is repeatedly performed, for example, and the processing returns to step S500 when it is detected that normal measurement is no longer possible. Alternatively, the position and distance may be repeatedly detected simply for every predetermined time (for instance, several seconds to several minutes).

Second Embodiment

Next, a second embodiment of the present disclosure will be described.

Although the configuration of the biological information detection device 100 in this embodiment is the same as the configuration in the first embodiment, the processing performed by the calculation circuit 200 are different between the first and second embodiments. In this embodiment, when the orientation of a test portion of the subject O is inclined with respect to a reference orientation, the calculation circuit 200 determines a target area for which biological information is generated, according to the magnitude of the inclination. In addition, the calculation circuit 200 adjusts the signal intensity of biological information according to the magnitude of the inclination. Hereinafter, the operation in this embodiment will be described using an example of the case where the cerebral blood flow in the cerebral cortex is measured using near-infrared light.

The calculation circuit 200 in this embodiment determines whether or not the normal direction of the center of the forehead serving as the test portion of the subject is inclined with respect to the front direction. When the normal direction is not inclined with respect to the front direction or the inclination is small, the target area for which biological information is generated is set to the center position of the forehead of the subject like the area enclosed by a dashed line in FIG. 4A. At this point, the target area does not have to be set to the center position of the forehead of the subject, and may be set to a position displaced upward, downward, rightward, or leftward from the center position of the forehead, for instance, according to the purpose of obtaining biological information. In FIG. 4A, the shape of the target area is set to substantially rectangular figure, however, may be set to, for instance, triangular figure, elliptical figure, or any other figure without being limited to rectangular figure. Furthermore, for instance, the shape of the target area may be a shape such that each side of a rectangle and others is curved correspondingly to the convexity of the forehead of the subject.

Figure 7A:
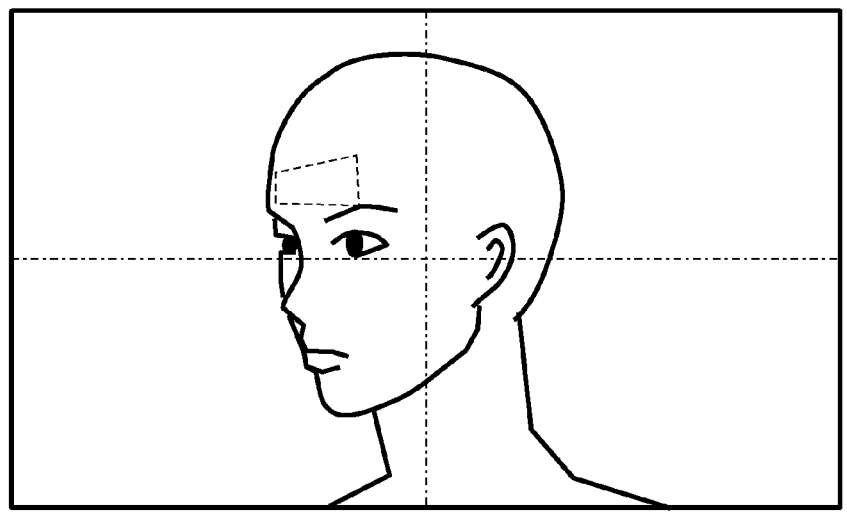
FIG. 7A is an illustration of an outline of an operation in a second embodiment.
Figure 7B:
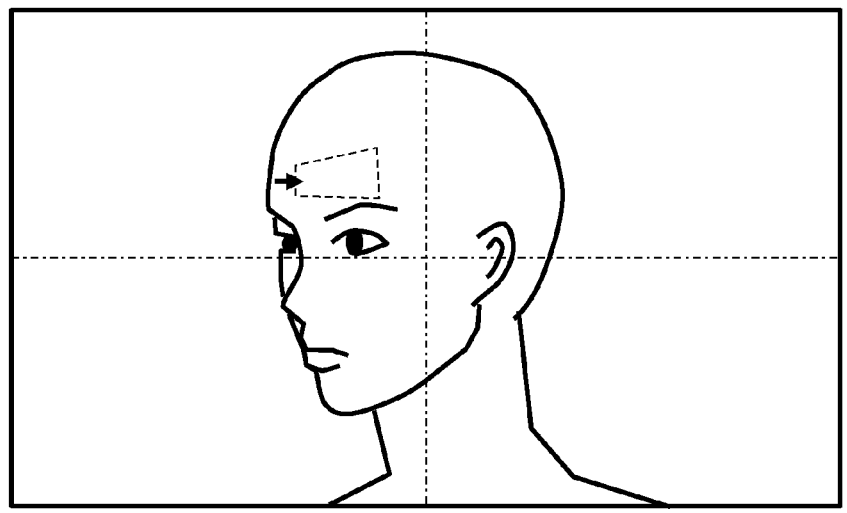
FIG. 7B is another illustration of the outline of the operation in the second embodiment.

FIGS. 7A and 7B are illustrations of an outline of the operation in this embodiment. As described above, the calculation circuit 20 in this embodiment determines whether or not the normal direction of the center of the forehead serving as the test portion of the subject is inclined with respect to the front direction. The determination of inclination is continuously performed, and when the magnitude of the inclination has changed from that at the moment of making the initial setting of the target area, the position (center position) and/or shape of the target area are modified according to the magnitude of the inclination after the change. As illustrated in FIGS. 7A and 7B, when the forehead as the test portion is inclined rightward with respect to the subject, the position of the target area is shifted to the left side of the forehead of the subject. Thus, the position of the target area may be shifted in a direction in which the target area is overall closer to the biological information detection device 100. FIG. 7A illustrates the target area before shifted by a dashed line, and FIG. 7B illustrates the target area after shifted by a dashed line. The amount of shift increases as the inclination angle of the test portion increases. Also, the shape of the target area may be changed according to the convexity of the forehead of the subject, for instance. The calculation circuit 200 performs such an operation when a target area is determined, which is a preceding step of generation of biological information in step S501 illustrated in FIG. 6. In this process, the signal intensity is also adjusted at the same time as necessary. Hereinafter, the operation will be described in more details.

Figure 8A:
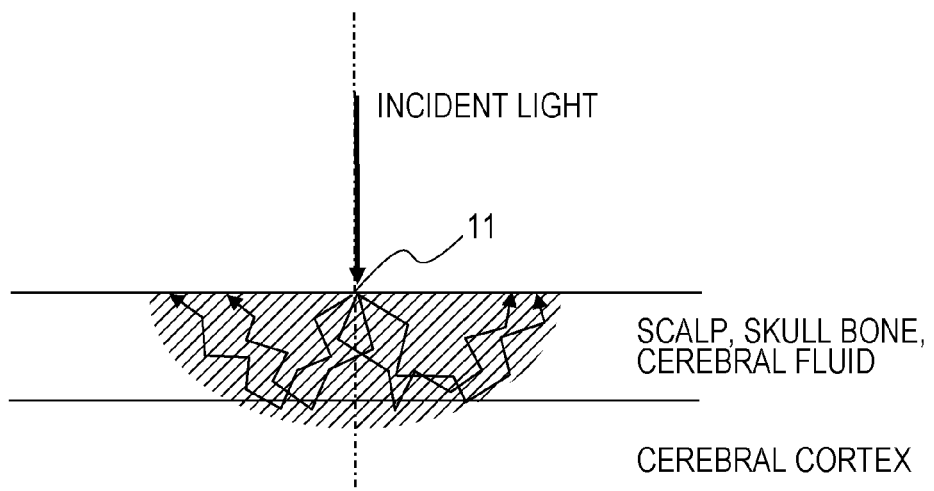
FIG. 8A is a diagram schematically illustrating a section of a head when seen from the top side of the head.
Figure 8B:
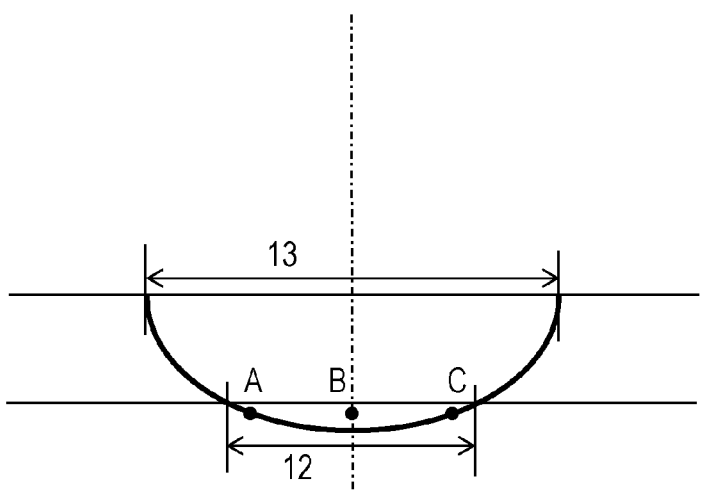
FIG. 8B is a diagram illustrating a measurement target portion for biological information on the cerebral cortex, and a light emitting portion which is an area on the skin surface and through which light is emitted in the state illustrated in FIG. 8A.

FIG. 8A is a diagram schematically illustrating a section of a head when seen from the top side of the head. For the sake of simplicity, in FIG. 8A, the portions of the scalp, skull bone, cerebral fluid in the sectional view of the head are collectively illustrated as one layer, and the portion of the cerebral cortex is illustrated as one layer. In addition, for the sake of simplicity of description, near-infrared light is illustrated as a ray of light that goes straight without a spread, and the near-infrared light seems to be emitted to a point of the test portion. Actually, however, near-infrared light has a diffused distribution, and thus the entire test portion is irradiated with the near-infrared light. In FIG. 8A, the arrows indicate an example of possible optical paths of near-infrared light, and the shaded portion indicates the area to which the near-infrared light incident from a light incident portion 11 can propagate. In the example of FIG. 8A, the subject O faces the front of the light detector 140 of the biological information detection device 100, and near-infrared light is perpendicularly incident on the skin surface. FIG. 8B illustrates a measurement target portion 12 for biological information on the cerebral cortex, and a light emitting portion 13 which is an area on the skin surface and through which light is emitted. FIG. 8B illustrates only the outline of a propagation area of near-infrared light.

When near-infrared light reaches the light incident portion 11 on the skin surface, the light is divided into two components: one is reflected by the skin surface and the other enters the inside of the head. In FIG. 8A, a component reflected by the skin surface is not illustrated. Since the skin surface is not actually flat, near-infrared light is diffusely reflected by depressions and projections on the surface. The inside of the head has a structure in which a plurality of different body tissues are layered. For this reason, until near-infrared light reaches the measurement target portion 12 in the cerebral cortex and the near-infrared light is radiated to the outside of the skin surface again, refraction, absorption, and scattering are repeated according to optical parameters (such as a refractive index, a scattering coefficient, an absorption coefficient and an anisotropic scattering parameter) specific in each tissue. As a result, the near-infrared light is emitted from the light emitting portion 13 which has a spread with the center at the light incident portion 11.

The depth inside the head to which near-infrared light reaches depends on the wavelength and intensity of the light. With the same wavelength, light with a higher intensity can reach a deeper position. However, when a living body is to be measured, so-intense near-infrared light cannot be used for the sake of safety. The emission power of the light source is normally set to an appropriate range in consideration of the safety. When a laser of class 1 is used as the light source, near-infrared light reaches a depth of approximately 20 to 30 mm, the light is absorbed and scattered by part of the cerebral cortex, and is emitted from the light emitting portion 13 in a range with a radius of approximately 30 mm at the center of the light incident portion 11. Like this, when information on a deep position inside an absorbing and scattering body is measured, the position of the measurement target portion 12 and the position of the light emitting portion 13 where a signal with the information is detected are not necessarily matched. The propagation optical path of near-infrared light can be estimated using a simulation such as Monte Carlo simulation based on the wavelength of the light, and optical parameters (such as a refractive index, a scattering coefficient, an absorption coefficient and an anisotropic scattering parameter) of body tissues.

Here, the effect of change in the incident angle of near-infrared light on the test portion will be described with reference to FIGS. 9A and 9B.

Figure 9A:
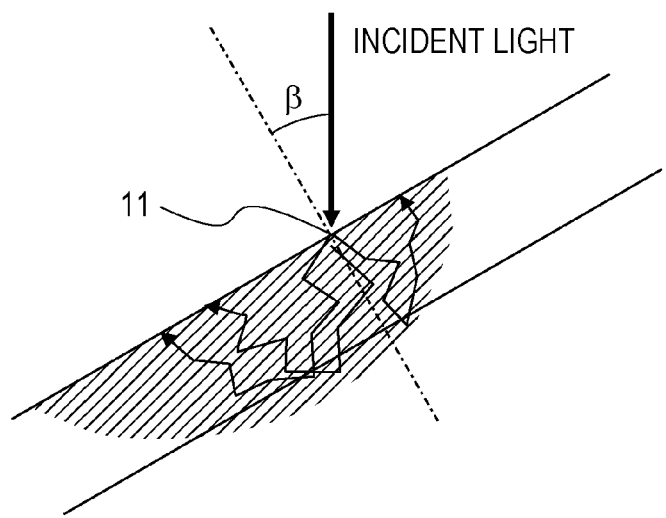
FIG. 9A is a sectional view illustrating a state where a test portion is inclined by an angle β in the state illustrated in FIG. 8A.

FIG. 9A is a sectional view illustrating a state where the test portion is inclined by an angle $\beta$ in the state illustrated in FIG. 8A. FIG. 9B illustrates a measurement target portion 22 for biological information on the cerebral cortex, and a light emitting portion 23 which is an area on the skin surface and through which light is emitted. Because light entering inside a living body is forward scattered, in the case where near-infrared light enters the skin surface with inclined to the skin surface, the distribution of scattered light is shifted to the far side (the left side in FIG. 9B) of the biological information detection device 100 compared with the case where near-infrared light perpendicularly enters the skin surface.

As illustrated in FIGS. 8A and 8B, when near-infrared light perpendicularly enters the skin surface, the near-infrared light mainly propagates through the light incident portion 11, passes through the measurement target portion 12 including points A, B, C of the cerebral cortex, and is radiated from the light emitting portion 13. In other words, near-infrared light with information on the points A, B, C of the cerebral cortex is radiated from the light emitting portion 13. With this detection, the biological information detection device 100 can obtain biological information.

Figure 9B:
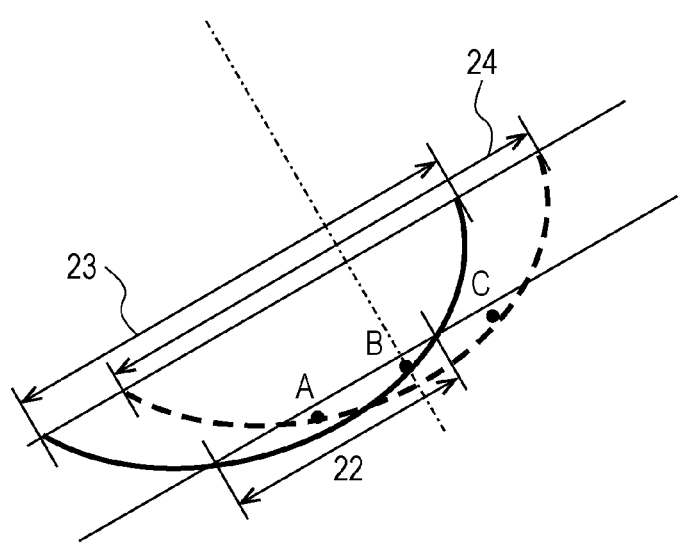
FIG. 9B is a diagram illustrating a measurement target portion for biological information on the cerebral cortex, and a light emitting portion which is an area on the skin surface and through which light is emitted in the state illustrated in FIG. 9A.

On the other hand, in the state illustrated in FIGS. 9A and 9B, near-infrared light enters the skin surface with an incident angle $\beta$. For this reason, the near-infrared light entering through the light incident portion 11 is scattered weakly in the backward direction and intensely in the forward direction with respect to the propagation direction. As a result, the near-infrared light does not reach the point C of the cerebral cortex, located on the near side as viewed from the light detector 140, but reaches the measurement target portion 22 including the points A, B located on the far side. The near-infrared light reaching the measurement target portion 22 is reflected by the measurement target portion 22, and is radiated from the light emitting portion 23 having a spread. Thus, even when the light emitted from the light emitting portion 23 is detected, the biological information at the point C cannot be obtained. In order to obtain information on an area including all the points A, B, C, near-infrared light emitted from a light emitting portion 24 on the near side of the light emitting portion 23 has to be detected.

Thus, when the orientation of the test portion is inclined with respect to the front direction, in other words, when the light from the light source 110 enters the test portion with an inclination, the calculation circuit 200 in this embodiment shifts the target area for which biological information is generated in a direction closer to the detector 140. Thus, it is possible to obtain biological information on the same area as in the case where the test portion faces the front.

Here, for the sake of simplicity of description, near-infrared light is assumed to be a ray of light without a spread. However, actually, near-infrared light has distribution with a spread. Thus, the calculation circuit 200 may identify the area on the skin surface, through which light having information on a target portion of the cerebral cortex is emitted, in consideration of the illumination intensity distribution of light emitted from the light source. The target area may be determined or shifted based on a result of the identification. Detection of near-infrared light emitted from thus identified area allows biological information with less noise to be obtained.

Figure 20:
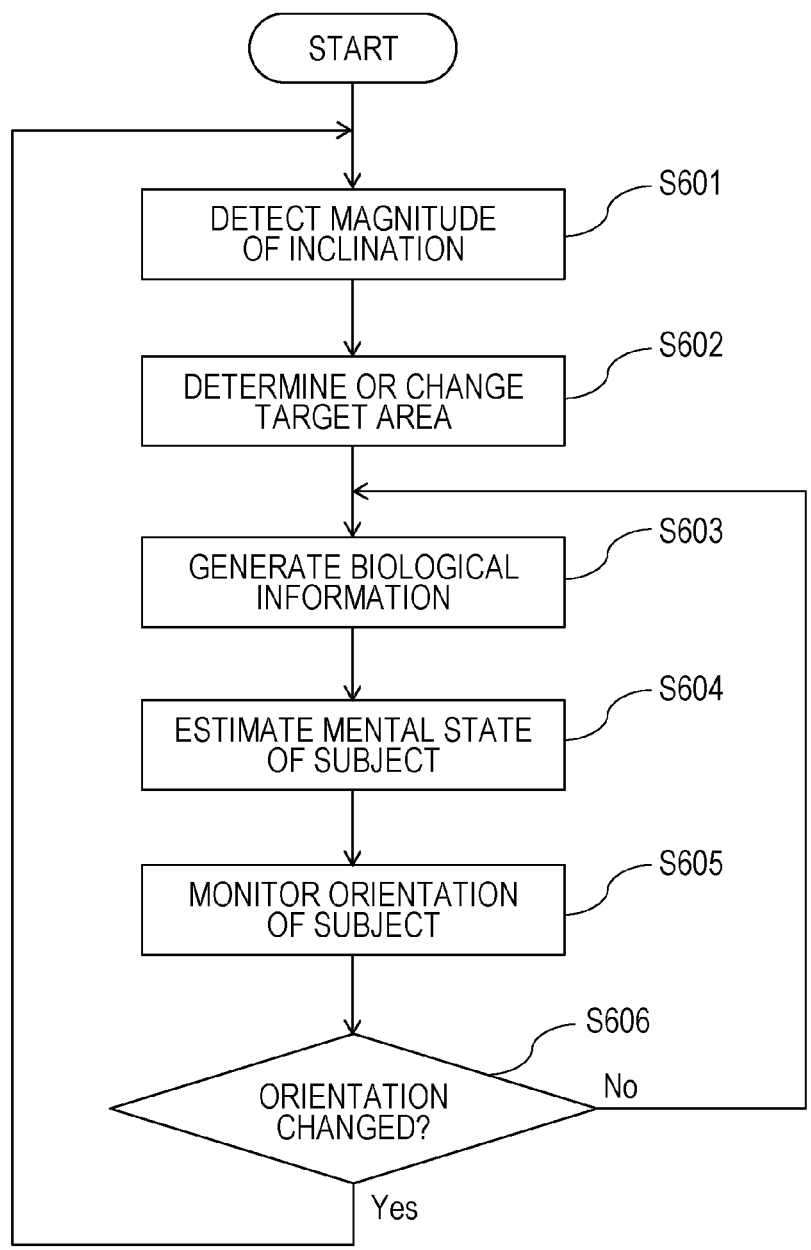
FIG. 20 is a flowchart illustrating an example of an operation of the biological information detection device in the second embodiment.

FIG. 20 is a flowchart illustrating an example of the operation of the biological information detection device 100 in the second embodiment. The operation of the biological information detection device 100 will be described using the flowchart. It is to be noted that description of a part redundant with the operation of the biological information detection device 100 in the first embodiment will be omitted.

(Step S601)

The calculation circuit 200 detects the orientation of the test portion (forehead) of the subject O based on the image signal outputted from the light detector 140. Here, the orientation of the test portion is, for instance, the normal direction of the center of the forehead of the subject. Specifically, the calculation circuit 200 identifies whether or not the forehead of the subject O is present in the frame image outputted from the light detector 140, and identifies the position of the forehead by image recognition. The calculation circuit 200 detects the position of the test portion and the orientation of the test portion based on the positions of the feature points (such as the eyes, nose and mouth) in the face. The magnitude of the inclination of the test portion is calculated based on the detected orientation of the test portion. The magnitude of the inclination of the test portion is the magnitude of the inclination of the test portion with respect to the reference orientation (the front direction).

(Step S602)

The calculation circuit 200 determines a target area in the test portion, for which biological information is generated, based on the magnitude of the inclination of the test portion calculated in step S601. When a target area is already set, the target area is changed according to the magnitude of the inclination of a newly detected test portion. The calculation circuit 200 may change the position of the target area or may change the shape of the target area.

(Step S603)

The calculation circuit 200 generates biological information on the target area in the image, which is determined or changed in step S602, based on the image signal outputted from the light detector 140. Specific processing is the same as in step S501, thus a description is omitted.

(Step S604)

The calculation circuit 200 estimates a mental state of the subject based on the biological information. Specific processing is the same as in step S503, thus a description is omitted.

(Step S605)

As described above, it is assumed that the subject O is learning by solving a problem, for instance. In this case, it is presumed that the head of the subject O, specifically, the forehead as a test portion moves during measurement. The orientation of the test portion is changed by the movement. Thus, the calculation circuit 200 monitors the orientation of the test portion all the time. For instance, the calculation circuit 200 continuously detects the orientation of the test portion based on the image signal outputted from the light detector 140.

(Step S606)

The calculation circuit 200 determines whether or not the orientation of the test portion being monitored in step S605 has changed. When it is determined that the orientation of the test portion has not changed (No in step S606), the processing proceeds to step S603, and biological information on the target area determined in step S602 is generated. When it is determined that the orientation of the test portion has changed (Yes in step S606), the processing proceeds to step S601, and the magnitude of the inclination of the test portion is detected. Subsequently, the processing is performed in accordance with the flowchart, and the target area is modified according to the magnitude of the inclination.

Next, the effect on an optical path length of near-infrared light due to a change in the inclination of the test portion is taken into consideration.

When the incident angle of near-infrared light is changed from 0° to β, the optical path length in the scalp and skull bone becomes (1/cos β) times longer. For this reason, frequency of light scattering and absorption increases, and there is a low probability that light is emitted through the skin surface again. In addition, the reflection rate and distribution of light on the skin surface or the interfaces of tissues change, and this causes a change in the probability and distribution that near-infrared light having information on the cerebral cortex is radiated to the skin surface. As a result, the intensity of the signal obtained by the light detector 140 is decreased compared with the case where the incident angle is 0°. When a temporal change in the cerebral blood flow of the cerebral cortex is observed, adjustment may be made to allow comparison between signals obtained at different times.

Thus, the calculation circuit 200 in this embodiment makes adjustment to allow comparison between pieces of biological information in consideration of changes in the propagation path and the detected signal intensity due to the incident angle of light. Specifically, the calculation circuit 200 performs the following processing:

(1) Detection of the face of the subject O, and identification of the orientation of the face.

(2) Estimation of the position of the cerebral cortex to be measured.

(3) Calculation of the propagation optical path of near-infrared light, and the probability and distribution that near-infrared light is radiated through the skin surface, based on the wavelength and the incident angle of near-infrared light, and the optical parameters (such as a refractive index, a scattering coefficient, an absorption coefficient and an anisotropic scattering parameter) of body tissues.

(4) Estimation of a light emitting portion through which near-infrared light having information on a portion of the cerebral cortex to be measured is radiated, and determination of a target area on the image, for which biological information is obtained.

(5) Prediction of the rate of increase or decrease (increase or decrease ratio) of the signal intensity of near-infrared light radiated from the light emitting portion, with respect to the signal intensity when the incident angle of light is 0 degree, for each of pixels or for each of pixel groups.

(6) Generation of biological information on the determined target area.

(7) Adjustment of biological information in accordance with the predicted increase or decrease ratio.

With such processing, even when the inclination of the test portion changes during detection of biological information, biological information which allows easy comparison can be obtained.

Here, for the sake of simplicity, description has been given under the assumption that the surface of a human head has a two-layer structure including the cerebral cortex and its upper tissues. However, the surface of an actual human head is not flat, the upper tissues have no uniform and homogeneous layer structure, and the structure of the cerebral cortex is also complicated and is individually specific. When sophisticated measurement analysis is necessary, the cerebral structure is measured by magnetic resonance imaging (MRI) or the like for each of subjects, and the propagation path of near-infrared light can be elaborately calculated in accordance with the actual shape. Alternatively, a more or less probable optical path can be calculated using a standard brain model with a lower accuracy. Selection of a method to be adopted should be made according to a time taken for calculation processing and the application and purpose.

When biological information is measured, calculation and estimation of a propagation path of near-infrared light are not necessarily performed. Once the biological information detection device 100 has learned general patterns of the orientation of face and the propagation path, just detection of the orientation (in other words, the incident angle of near-infrared light on the test portion) of the face allows information on the propagation path to be obtained. Thus, it is possible to estimate the position of the light emitting portion and the increase or decrease ratio of the signal, and to adjust the obtaining position of biological information and the signal intensity.

Like this, the calculation circuit 200 can predict the intensity of the light emitted from the test portion or the rate of change (increase or decrease ratio) in the intensity with respect to a reference value based on at least one of the inclination of the test portion and the predicted propagation path. When the predicted intensity or the rate of change in the intensity is smaller than a predetermined value (a first threshold value), the calculation circuit 200 increases the signal intensity and outputs the signal. On the other hand, when the predicted intensity or the rate of change in the intensity is larger than another predetermined value (a second threshold value), the calculation circuit 200 decreases the signal intensity and outputs the signal.

So far, a method of simulating a propagation path of near-infrared light, adjusting the obtaining position of biological information and adjusting the signal intensity of biological information have been described. However, adjustment can be made based on actually measured data. For instance, prior learning may be made in which measurements are made with various angles in a state of the same brain activity and in order to achieve matching with measurement results at a reference angle, an amount of displacement of each of feature points of the face and an adjustment coefficient of the signal intensity at other angles are determined. Once such prior learning is made, the biological information detection device 100 can determine the position of the target area and the increase or decrease ratio by detecting the distance to and orientation (inclination angle) of the test portion.

Third Embodiment

Figure 10:
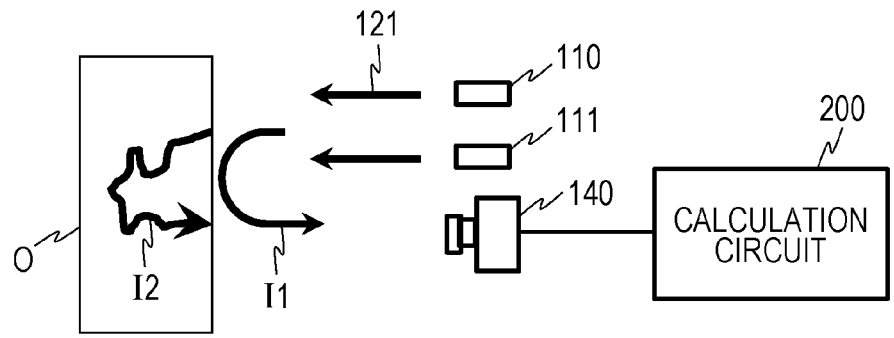
FIG. 10 is a diagram schematically illustrating a configuration of a biological information detection device in a third embodiment.

FIG. 10 is a diagram schematically illustrating a configuration of a biological information detection device in a third embodiment of the present disclosure. The biological information measuring device in the present embodiment includes two light sources 110, 111. The two light sources 110, 111 are connected to the calculation circuit 200.

The light sources 110, 111 emit light with different wavelength ranges. The wavelengths of the light emitted by the light sources 110 and 111 may be, for instance, 650 nm and 830 nm mentioned above. However, without being limited to this combination of wavelengths, various combinations may be adopted. In the case where an object to be measured is a body tissue as in this embodiment, when the wavelength is greater than 805 nm, as illustrated in FIG. 2, the absorbance of oxyhemoglobin is higher than the absorbance of deoxyhemoglobin. On the other hand, when the wavelength is less than 805 nm, the opposite property is exhibited. Now, for instance, the light source 110 is assumed to emit light with a wavelength near 750 nm, and the light source 111 is assumed to emit light with a wavelength near 850 nm. In this case, when the light power of each of the internal scattering component 12 due to the light from the light source 110 and the internal scattering component 12 due to the light from the light source 111 is measured, the amounts of change from the initial values of the concentrations of $HbO_2$ and Hb in blood can be determined by solving a predetermined simultaneous equations.

The calculation circuit 200 calculates, for instance, the amounts of change from the initial values of the concentrations of $HbO_2$ and Hb in blood by solving the simultaneous equations using the light power of each of the internal scattering component 12 due to the light from the light source 110 and the internal scattering component 12 due to the light from the light source 111. Independently from the calculation circuit 200, a calculation circuit (not illustrated), which solves the simultaneous equations, may be separately provided.

Although the number of light sources is two in the above example, three or more light sources having different wavelength ranges of emission light may be used. Alternatively, a light source having a changeable wavelength range of light may be used. Such a configuration allows more biological information on blood to be obtained.

Figure 11:
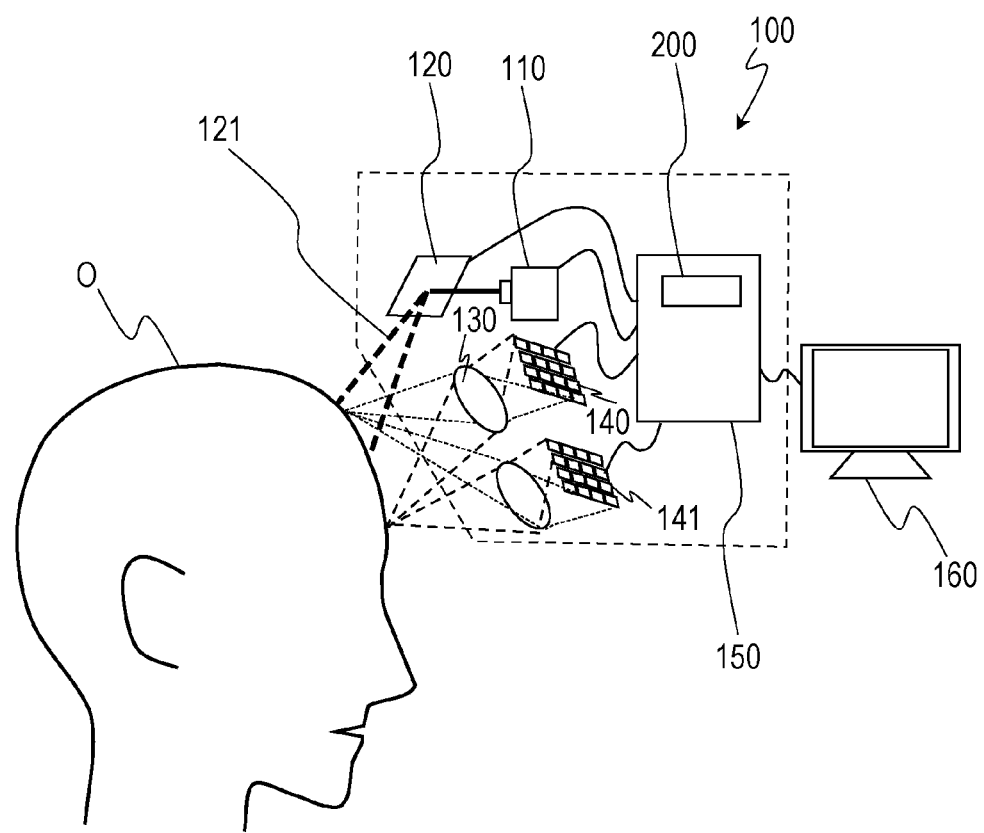
FIG. 11 is a diagram schematically illustrating a configuration example of the biological information detection device further including an image sensor separately from the light detector.

FIG. 11 is a diagram schematically illustrating an configuration example of the biological information detection device 100 further including an image sensor 141 separately from the light detector 140. Like this, the biological information detection device 100 may include another image sensor 141 independent from the light detector 140. With this configuration, the light detector 140 is used as a sensor that specializes in, for instance, biological information measurement. The position of and distance to a test portion can be detected based on the output signal from the image sensor 141. The calculation circuit 200 may detect movement of the subject using moving images based on the output signal of the image sensor 141. Alternatively, the calculation circuit 200 may detect the distance based on the output signal of the light detector 140, and may detect the position based on the output signal of the image sensor 141, or the calculation circuit 200 and the light detector 140 may switch functions. In the present description, the light detector 140 may be referred to as the "first light detector", and the image sensor 141 may be referred to as the "second light detector". Also, an electrical signal outputted from the first light detector may be referred to as a "first electrical signal", and an electrical signal outputted from the second light detector may be referred to as a "second electrical signal".

The biological information detection device 100 according to this embodiment can measure biological information other than the cerebral blood flow. Some specific examples will be described below.

When the blood flow rate changes, the reflectivity of light changes. Utilizing this, exposed test portions such as the face and hand are irradiated with near-infrared light and reflected light is detected, thereby making it possible to measure a pulse rate and a level of concentration in a non-contact manner. According to the above-described flowchart illustrated in FIG. 6, the control circuit 200 detects the position and distance at a test portion, and can subsequently adjust the signal intensity of biological information.

Figure 12:
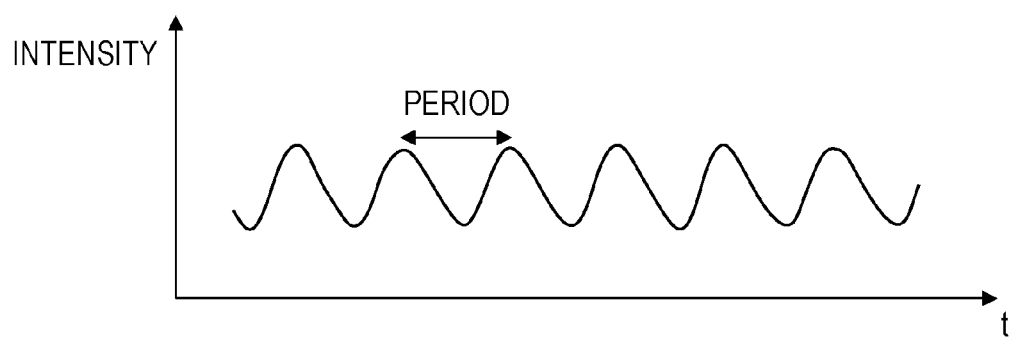
FIG. 12 is a diagram schematically illustrating an example of a pulse wave obtained by measurement.

FIG. 12 is a diagram schematically illustrating an example of a pulse wave obtained by measurement. When a pulse rate is measured, the calculation circuit 200 generates a pulse wave having a periodic curve based on, for instance, the output signal from the light detector 140. For instance, the calculation circuit 200 identifies the local maximum values of pulse waves, and as illustrated, calculates the time difference (referred to as the "period of pulse wave") between two adjacent local maximum values. The calculation circuit 200 calculates a pulse rate by converting the period of pulse wave to a reciprocal.

The calculation circuit 200 measures the variance of the period of pulse wave in a predetermined time period, and can determine a mental state such as a concentrated state and a relaxed state. In general, in a concentrated or nervous state, the period of pulse wave tends to be uniform, whereas in a relaxed state, the period of pulse wave tends to vary. Thus, when the variance of the period is less than a predetermined value, the calculation circuit 200 determines that the subject O is in a concentrated state or in a nervous state. With the breathing, the variance may gradually increase and exceed a predetermined value. In this case, the calculation circuit 200 may determine that the subject O is in a relaxed state.

In addition, aging of blood vessels and a blood pressure can be measured by using the biological information detection device 100 in a non-contact manner. Specifically, a pulse wave velocity (PWV) is measured by using the biological information detection device 100. Pulse waves at the face or hand are measured, and PWV is obtained by dividing the distance between them by the time difference between the pulse waves.

For instance, the PWV can be determined by irradiating two exposed test portions of the face and hand with near-infrared light, and detecting reflected light. Alternatively, the PWV can be determined by irradiating, for instance, two exposed test portions of a hand and ankle with near-infrared light, and detecting reflected light. It is to be noted that as two test portions, any points spaced apart may be designated. It is possible to measure aging of blood vessels and a blood pressure based on the PWV in a non-contact manner. According to the above-described flowchart illustrated in FIG. 6, the calculation circuit 200 detects the positions and distances at two test portions, and subsequently adjusts a signal level of biological information properly.

Figure 13:
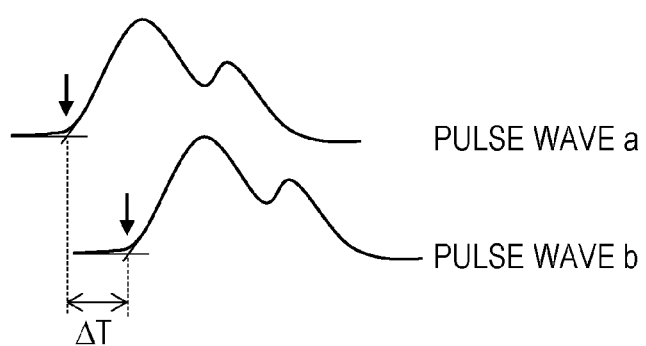
FIG. 13 is a diagram schematically illustrating pulse waves obtained from two points of the face and hand.

FIG. 13 schematically illustrates pulse waves a, b obtained from, for instance, two points of the face and hand. A measurement point A is positioned on the face and a measurement point B is positioned on a hand. For instance, the calculation circuit 200 calculates PWV from the following Expression (1) using a time difference $\Delta T$ between the rising edges (indicated by arrows in FIG. 13) of the pulse waves at the measurement points A and B, and the distance D between the measurement points A and B:

$$\text{PWV}=D/\Delta T \qquad \text{Expression (1)}.$$

The calculation circuit 200 can estimate aging of blood vessels and a blood pressure based on the PWV. For instance, a table indicating the average value of PWV for each age (generation) is pre-stored in the ROM 152. The calculation circuit 200 refers to the table to identify the age for which the average PWV value is the closest to the PWV value obtained by the measurement, and can estimate aging of the blood vessels of the subject O. Also, the calculation circuit 200 can estimate a blood pressure from the PWV. For instance, it is possible to utilize the method of estimating a blood pressure using PWV, disclosed in G. Lopez et al. "Continuous blood pressure monitoring in daily life," Journal of Advanced Mechanical Design, Systems, and Manufacturing 3(1), 179-186 (2010).

When a contact measuring instrument is used, how the sensor portion is attached to or pressed against the body may affect to the result of measurement. When measurement is made in a non-contact manner as in this embodiment, such a problem is solved, which leads to simplified measurement.

According to this embodiment, the calculation circuit 200 properly adjusts the signal intensity of biological information according to the position of and distance to a test portion. Consequently, during the measurement, the subject O is not restrained by the device and can spend time in a relatively relaxed posture. Also, since a high quality signal can be obtained, the SN ratio can be improved. Furthermore, since the calculation circuit 200 monitors the movement of the subject O, even when the subject O moves slightly during the measurement, stable measurement of biological information is possible. Thus, the subject O can undergo measurement while doing some work, for instance.

Fourth Embodiment

Next, a biological information measuring module in a fourth embodiment will be described. The biological information measuring module in this embodiment is an attachment that is externally mounted on a general-purpose mobile electronic device such as a tablet terminal, a smartphone, and a notebook PC (laptop), for instance. Hereinafter, the features of the biological information detection device 100 according to the second embodiment, different from the features of the biological information detection device 100 in the first embodiment will be mainly described, and a description of common features is omitted.

Figure 14A:
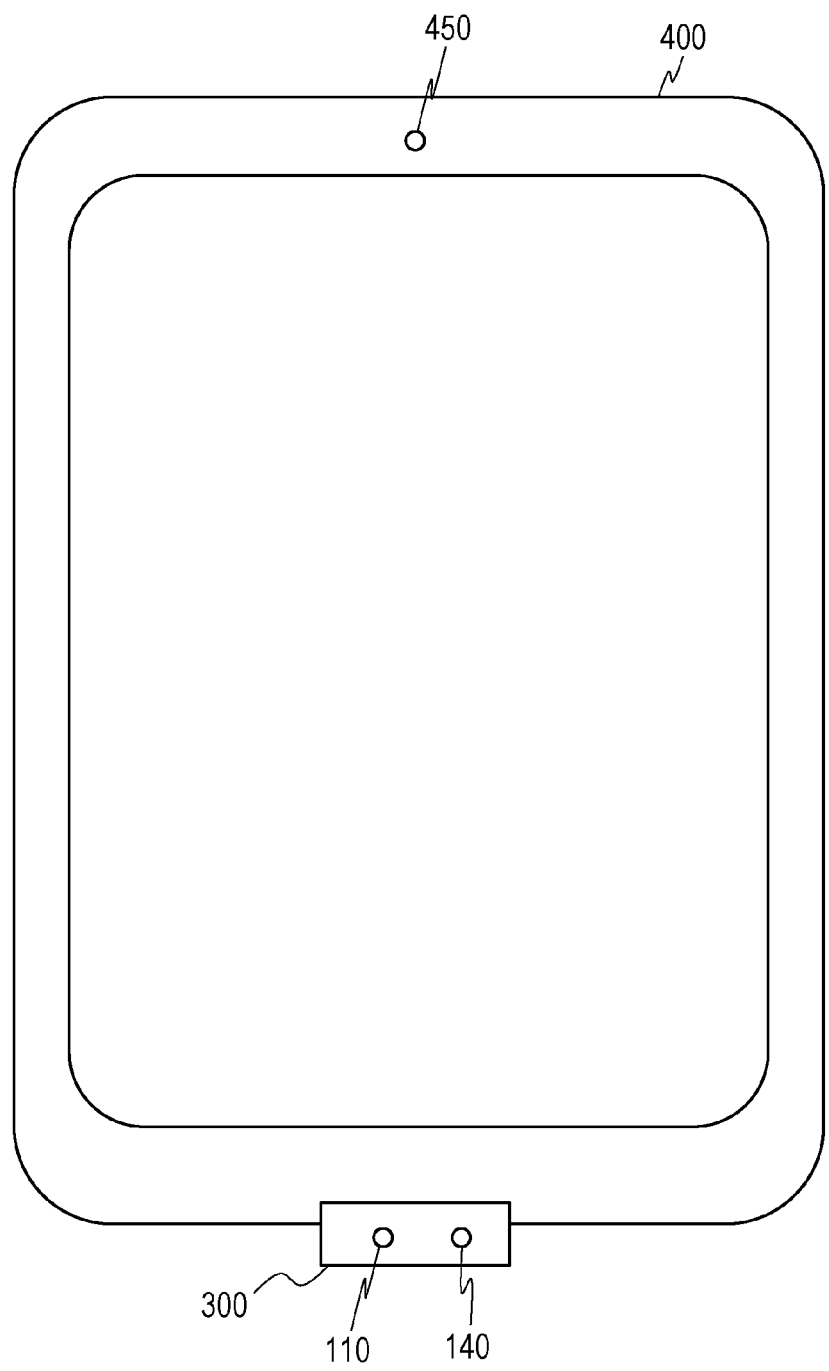
FIG. 14A is a diagram schematically illustrating an example of an electronic device equipped with a biological information measuring module in a fourth embodiment.

FIG. 14A schematically illustrates an example of an electronic device 400 including a biological information measuring module 300 in this embodiment. As illustrated, the biological information measuring module 300 is connected to the electronic device 400 and used. The module 300 has the light source 110 and the light detector 140. Although not illustrated in FIG. 14A, the optical element 120 such as a MEMS mirror, and a control circuit are provided in the case of the module 300. Although the module 300 is connected to a lower portion of the electronic device 400 in the example of FIG. 14A, the embodiment is not limited to this. The position to be connected depends on the position of a connector included in the electronic device 400. In this embodiment, it is possible to utilize the information on moving images obtained by a camera 450 included in the electronic device 400. In addition, using a signal processing circuit (calculation circuit) included in the electronic device 400, generation and adjustment processing of the biological information which is same as that in any of the first to third embodiments can be performed.

This configuration allows a new application method in which the module 300 including, for instance, the light source 110 and the light detector 140 which specializes in biological information measurement (in other words, detects infrared light) is mounted on the electronic device 400 such as a tablet terminal and a smartphone. The following operations may be performed: the built-in camera 450 of the electronic device 400 detects the position of a test portion and the movement of the subject O, and the control circuit in the module 300 adjusts the emission direction and power of the light source 110 based on a signal detected.

In the built-in camera 450 of a device such as a tablet terminal and a smartphone, the front surface of an image sensor is normally provided with an infrared (IR) cut filter. Thus, the camera 450 cannot receive infrared light. On the other hand, in order to detect near-infrared light suitable for measurement of biological information, the light detector 140 of the module 300 does not include an IR cut filter but may include a visible light cut filter instead. Thus, biological information may be detected by the light detector 140 of the module 300, and the position and distance of a test portion, which are detectable even by visible light, may be identified by the camera 450 of the electronic device 400.

Figure 14B:
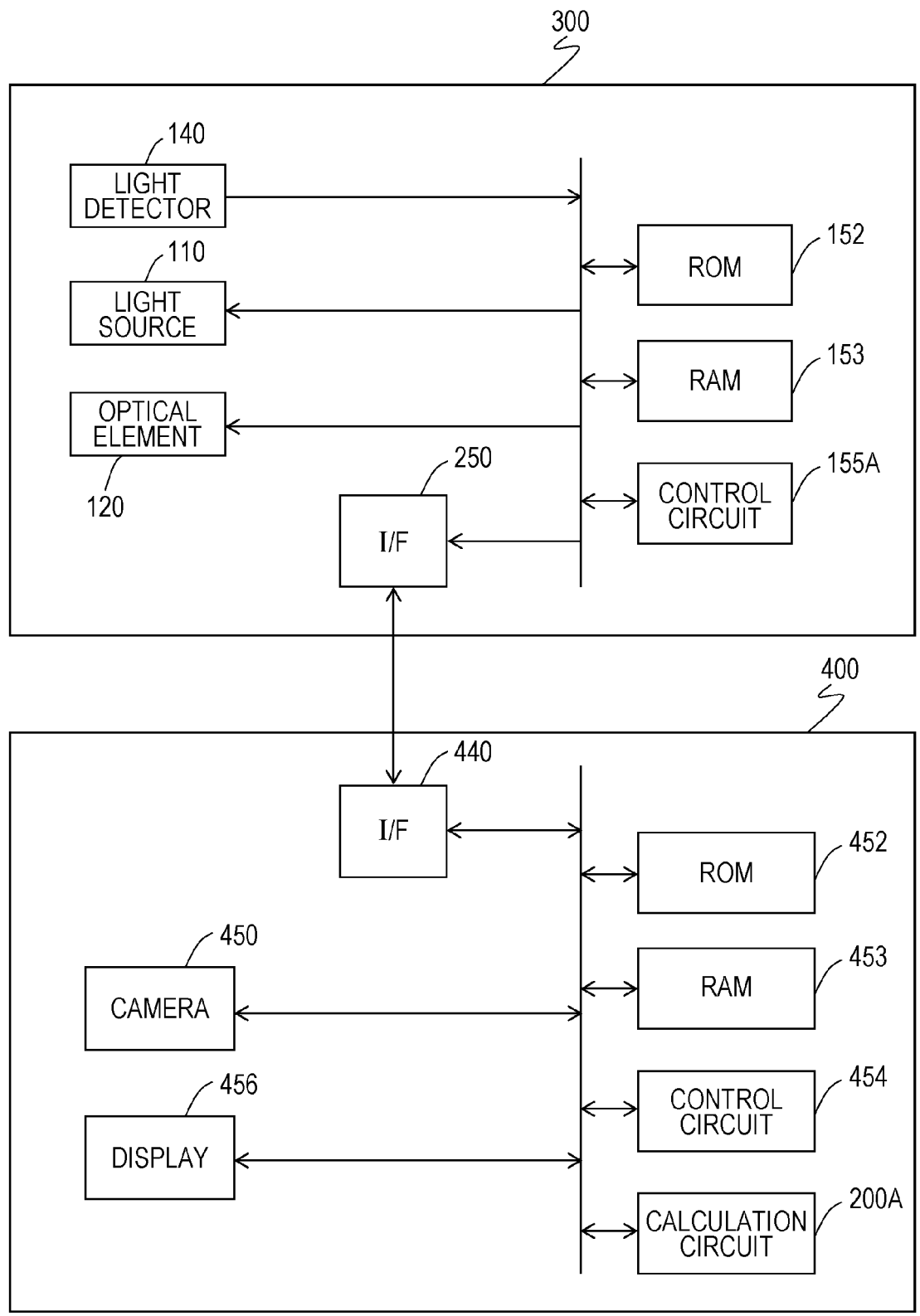
FIG. 14B is a block diagram schematically illustrating configurations of the biological information measuring module and the electronic device in the fourth embodiment.

FIG. 14B is a block diagram schematically illustrating the configurations of the biological information measuring module 300 and the electronic device 400 in this embodiment. The biological information measuring module 300 has the light source 110, the optical element 120, the optical system 130 (not illustrated), the light detector 140, the control circuit 155A, the ROM 152, the RAM 153, and an input/output interface (I/F) 250 for transmitting an output signal of the light detector 140 to the external electronic device 400. As illustrated, it is sufficient that the module 300 include a minimum number of components to operate as a module.

The electronic device 400 includes a display 456, a control circuit 454, a calculation circuit 200A, a ROM 452, a RAM 453, and an input/output interface 440 in addition to the camera 450. The control circuit 454 is a CPU, for instance, and the calculation circuit 200A may include a digital signal processor (DSP) for image processing, for instance. The calculation circuit 200A analyzes the image obtained by the camera 450. The control circuit 454 controls displaying of the display 456. The control circuit 454 and the calculation circuit 200A execute a pre-installed computer program (application), thereby performing an operation in cooperation with the module 300. For instance, the control circuit 454, when performing a measurement operation on biological information, causes the control circuit 155A of the module 300 to measure biological information using the light source 110, the optical element 120, and the light detector 140. At the same time, the control circuit 454 causes the camera 450 to capture the subject O, and causes the calculation circuit 200A to perform calculation of the position of and distance to the test portion and generation of biological information. The processing performed by the calculation circuit 200A is as described in first to third embodiments.

The output I/F 250 may be, for instance, a USB interface. The output I/F may be another interface, for instance, an interface for wireless communication in accordance with the W-Fi® standard or the ZigBee® standard.

The biological information measuring module 300 is connectable to the external electronic device 400 via a USB cable connected to the output I/F 250, for instance. An application is installed to the electronic device 400, the application for executing the signal processing (for instance, processing indicated in FIG. 6) in the present disclosure. Thus, the processor of the electronic device 400 (including the control circuit 454 and the calculation circuit 200A) receives an output signal of the light detector 140 from the biological information measuring module 300, and can measure biological information based on the output signal. Also, a mental state of the subject can be estimated based on the biological information.

According to this embodiment, there is provided a biological information measuring module which is detachably attachable to the external electronic device 400.

Fifth Embodiment

Next, an embodiment of a learning system that uses the technique in the present disclosure will be described.

Figure 15A:
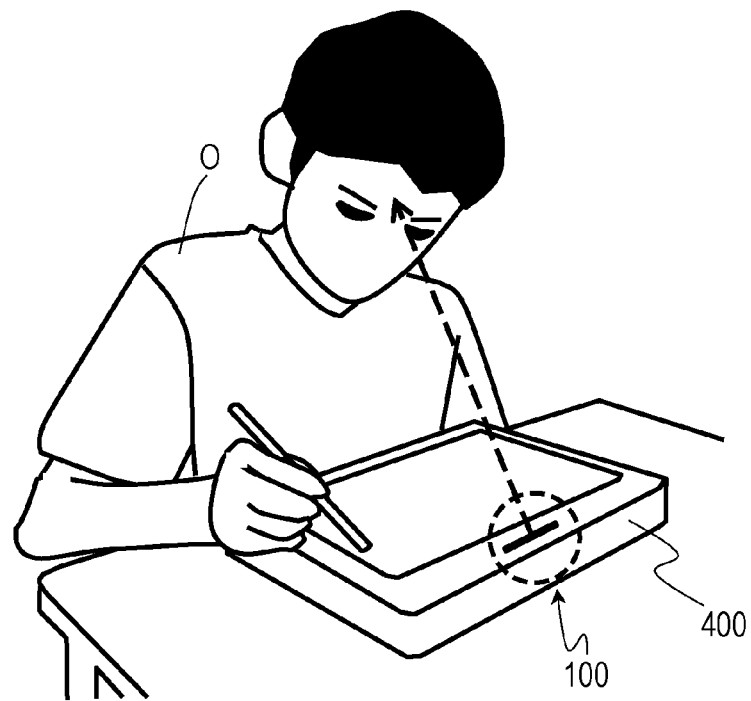
FIG. 15A is an illustration depicting a manner in which a learner as a subject is solving a problem of an academic subject (for instance, mathematics or national language) using an electronic device in a fifth embodiment.

FIG. 15A is an illustration depicting a manner in which a learner O as a subject is solving a problem of a subject (for instance, mathematics or national language) using the electronic device 400. The electronic device 400 in this embodiment is a tablet-type computer (hereinafter referred to as a tablet PC). In addition to a tablet PC, the electronic device 400 may be any device having a display, such as a mobile phone, a smartphone, a notebook PC (laptop), a digital book terminal, an electronic dictionary, and an electronic note.

The electronic device 400 may be a general-purpose terminal to which the module 300 in the fourth embodiment is mounted, or may be a dedicated terminal in which the function of the module 300 is incorporated.

The education system using a tablet PC as illustrated may be used, for instance, in an educational institution such as a school and a private tutoring school, or a home. The learner O (for instance, pupil) learns using application that displays problems of a subject such as mathematics and national language on a display of a tablet PC.

Application (software), which displays problems of a subject, is pre-installed to the electronic device 400. The application may be downloaded via an electrical communication line such as the Internet. The application is executed by the processor of the electronic device 400 (including the control circuit and the calculation circuit), thereby achieving the following operations: displaying a problem, displaying a correct answer and explanation after the problem is answered, and moving on to the next problem.

The control circuit of electronic device 400 in this embodiment monitors the level of concentration of a learner O by detecting biological information such as the cerebral blood flow rate, oxygen saturation in blood, and variance of the period of pulse wave while the learner O is solving a problem. The method of determining a level of concentration is as described in the first embodiment. The control circuit of the electronic device 400, when detecting a decrease in the level of concentration of the learner O, displays information to capture the learner's attention on the display, displays an easy problem, for an instance, to try to avoid decrease in the level of concentration. This can enhance the learning effect.

Figure 15B:
FIG. 15B is an illustration depicting an example of a state where the head of the learner has moved in the state of FIG. 15A.

In the learning system as in this embodiment, the learner O is not necessarily always sitting still while solving a problem. In particular, when the learner O doesn't know how to solve a problem, or lacks concentration, the head and the body of the learner O tend to move. FIG. 15B illustrates an example of a state where the head of the learner O has moved in the state of FIG. 15A. When the head of the learner O moves, the distance between the electronic device 400 and the test portion (forehead) may also change. In such a case, the conventional technique has a problem in that light from a light source does not reach the forehead or even when the light reaches the forehead, the detection accuracy decreases due to a change of the distance.

On the other hand, the calculation circuit of the electronic device 400 in this embodiment: detects the position of the forehead of the learner O, the distance to the forehead, and the inclination angle of the forehead; adjusts the emission direction and power of light according to the position, the distance, and the inclination angle; and adjusts properly the signal intensity of biological information. Thus, a level of concentration can be appropriately measured. For instance, such adjustment is made at the start of light-emission of the light source and for every predetermined time during light-emission, thereby making it possible to generate proper biological information all the time while keeping track of the movement of the forehead.

The electronic device 400 in this embodiment includes the biological information detection device 100 in any of the first to third embodiments. The electronic device 400 irradiates the forehead of the subject O with infrared light, and estimates a level of concentration in learning of the subject O utilizing the NIRS. The subject O learns by solving a problem displayed on the display screen of the electronic device 400 while manipulating on screen with a stylus. As described above, while the subject O is solving the problem, the cerebral blood flow rate etc. changes according to a level of concentration of the subject O by the activity of nerve cells. The calculation circuit 200 estimates a level of concentration of the subject O based on the change. For instance, a level of concentration may be determined by referring to a table as described above.

In addition, a level of mastery of learning can be determined by a temporal change of the level of concentration. Description is given by taking learning of factorization in mathematics as an example. At the beginning of learning, a subject learns a factorization formula and application of the formula. In the beginning, since the subject is not getting used to the formula, the level of concentration is high and the amount of temporal change in the cerebral blood flow rate is large. Since the subject gets used to application of the formula, as more problems are solved, the answering time decreases as well as the amount of temporal change in the cerebral blood flow rate decreases. It is possible to determine a mastery level of learning based on the temporal transition of a variation curve of the cerebral blood rate. Use of information indicating a degree of reduction of the answering time in addition to the temporal transition of change in the cerebral blood flow increases the accuracy of determination.

It is expected that the amount of movement of the head of the subject O as a user of the electronic device 400 varies according to the difficulty of the problem. For instance, it is assumed that when the subject O is solving a problem, the angle of the head changes from the angle illustrated in FIG. 15A to the angle illustrated in FIG. 15B. Even in this case, since the calculation circuit 200 is monitoring the movement of the subject O, detection of a movement allows the signal intensity of biological information to be adjusted.

According to this embodiment, even with the subject O doing some work, an appropriate position in the test portion can be irradiated with light and biological information can be measured stably.

Sixth Embodiment

Next, an interactive robot in a sixth embodiment will be described.

Figure 16:
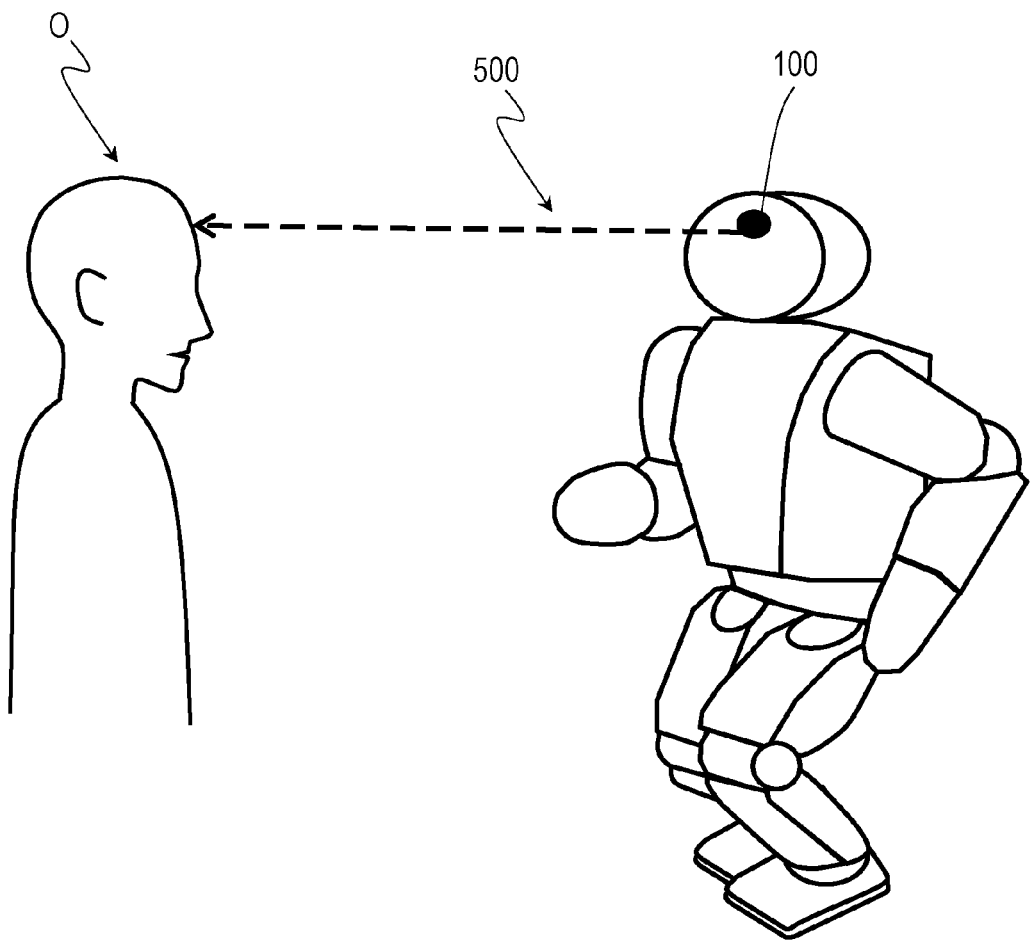
FIG. 16 is an illustration schematically depicting a robot and a conversation partner as a subject according to a sixth embodiment.
Figure 17:
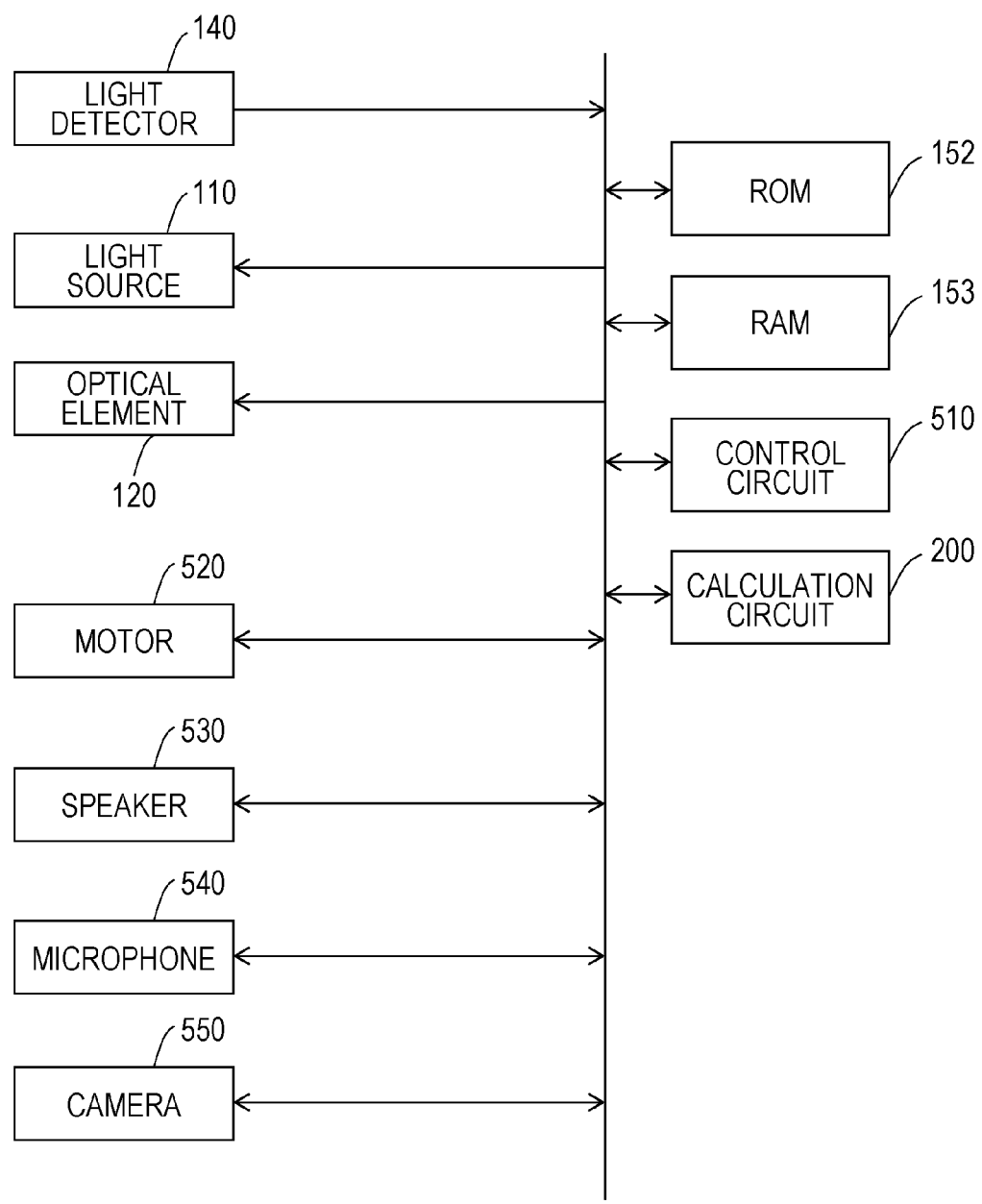
FIG. 17 is a diagram illustrating a configuration example of the robot.

FIG. 16 is an illustration schematically depicting a robot 500 and a conversation partner O as a subject according to the sixth embodiment. FIG. 17 is a diagram illustrating a configuration example of the robot 500.

The robot 500 in this embodiment has a head that includes the same components as in the biological information detection device 100 in any of the first to third embodiments. The robot 500 detects the position and distance of the forehead of the subject O, irradiates the forehead with light, and generates biological information of the subject O utilizing the NIRS to estimate the emotion. The robot 500 can adjust the irradiation position of light by moving its head while keeping track of the movement of the subject O. Since the robot 500 faces in the direction of the subject O during a conversation, adjusting the irradiation position of light by moving the head is a natural action.

As illustrated in FIG. 17, in addition to the components described in the first embodiment, the robot 500 includes at least one motor 520 that drives each part including the head, a speaker 530 that outputs voice, a microphone 540 that detects the voice uttered by the conversation partner O, a camera 550, and a control circuit 510 that controls each part. Also in this embodiment, the calculation circuit 200 detects the position of a test portion (for instance, the forehead) of the conversation partner O and the distance to the test portion by performing the same operations as those of the calculation circuit 200 in any of the first to third embodiments. The control circuit 510 then measures biological information such as the cerebral blood flow rate based on a result of the detection of the light detector 140. The control circuit 510 then generates a control signal for controlling an element such as the motor 520 and the speaker 530 based on the biological information. The robot 500 can perform various operations based on the control signal. For instance, when a decrease in the level of concentration of the conversation partner O is detected during a voice conversation using the speaker 530 and the microphone 540, the subject of the conversation may be changed or the voice conversation may stopped. During a conversation, the robot 500 estimates the emotion of the conversation partner O. Specifically, the calculation circuit 200 estimates the emotion based on a change in the cerebral blood flow caused by neural activity. For instance, the calculation circuit 200 can estimate the emotion by referring to a table that associates a change in the cerebral blood flow with an emotion (such as relief, anxiety, sadness and anger). The robot 500 can change the subject with the conversation partner, for instance, according to a result of the estimation of the emotion.

The control circuit 510 can adjust the emission direction of light by controlling the movement of the head according to the position of and distance to the test portion. Furthermore, the emission direction of light may be controlled by combining the head of the robot 500 and the optical element 120 disposed in front of the light source 110. For instance, the movement of the head is first controlled to generally adjust the emission direction of light, then the light source unit 170 is controlled, and the emission direction of light can be finely adjusted. The optical element 120 may not be provided if unnecessary.

A program (application), which defines the operations of this embodiment, is downloaded, for instance, via an electrical communication line and may be installed to the robot 500. Thus, the operation can also be improved by updating the application.

According to this embodiment, appropriate communication can be established in a conversation with a robot.

Seventh Embodiment

Figure 18:
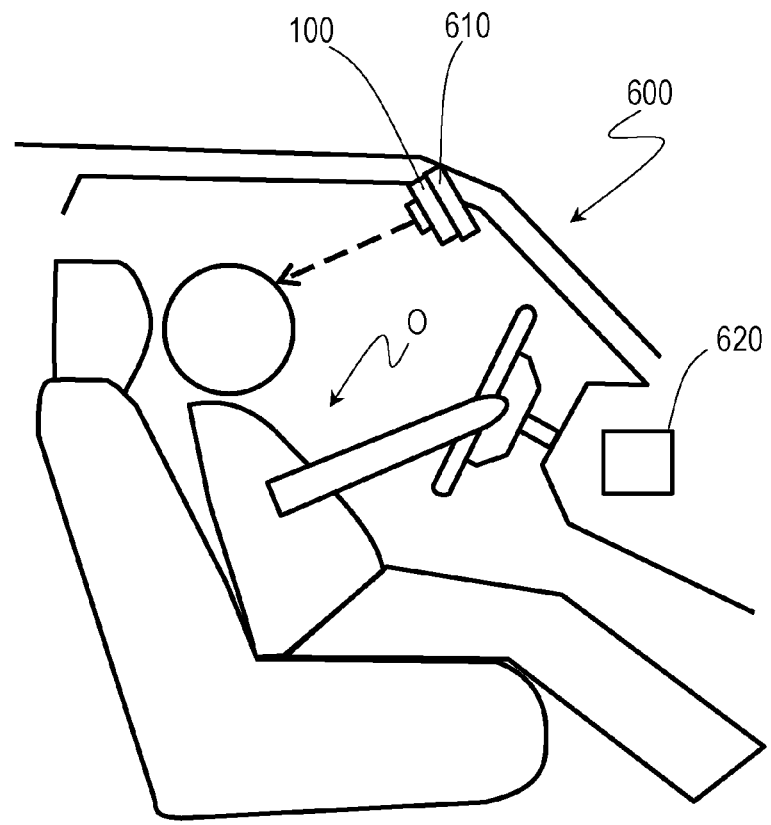
FIG. 18 schematically illustrates the inside of a vehicle according to a seventh embodiment.

FIG. 18 schematically illustrates the inside of a vehicle 600 according to a seventh embodiment.

The vehicle 600 according to this embodiment includes a biological information detection device 100 in the embodiment at a position or its vicinity where, for instance, a drive recorder is attached. The biological information detection device 100 may be attached to an attachment portion 610 of the vehicle 600. A driver can attach or detach the biological information detection device 100 freely. The vehicle 600 refers to not only an automobile but also a mobile object which needs to be operated, such as a train and others. In this embodiment, the subject O is a driver.

The biological information detection device 100 irradiates the forehead of the subject O with infrared light, and estimates a level of concentration or physical condition of the subject O utilizing the NIRS. The vehicle 600 includes a control circuit 620 that controls the operation of the vehicle 600. The control circuit 620 generates a control signal of the vehicle 600 based on the biological information from the calculation circuit 200 of the biological information detection device 100. Alternatively, the calculation circuit 200 may generate a control signal of the vehicle 600 based on the biological information, and the control circuit 620 may control the vehicle 600 based on the control signal. The vehicle has an automatic operation mode, for instance. During driving of the vehicle by manual operation, the vehicle receives a control signal, and can switch the driving mode from manual operation to automatic operation. For instance, when a decrease in the level of concentration of the driver O is detected, the driver O may be drowsy. Thus, switching from manual operation to automatic operation ensures the safety.

It is also possible to operate the biological information detection device 100 in conjunction with a car navigation system. For instance, the biological information detection device 100, when determining that the driver lacks concentration, can transmit relevant information to the car navigation system. The car navigation system can warn of the lack of concentration using a voice speaker or a display screen, for instance. It is to be noted that the biological information detection device 100 does not need to irradiate the driver with infrared light all the time, and for instance, a direction (such as "turn right at the intersection 100 m ahead") of the car navigation system may trigger the biological information detection device 100 to irradiate the driver with infrared light to determine the concentration level of the driver. When no change in the cerebral blood flow is detected even after voice directions are given by the car navigation, it is highly probable that the driver lacks concentration.

Eighth Embodiment

Figure 19:
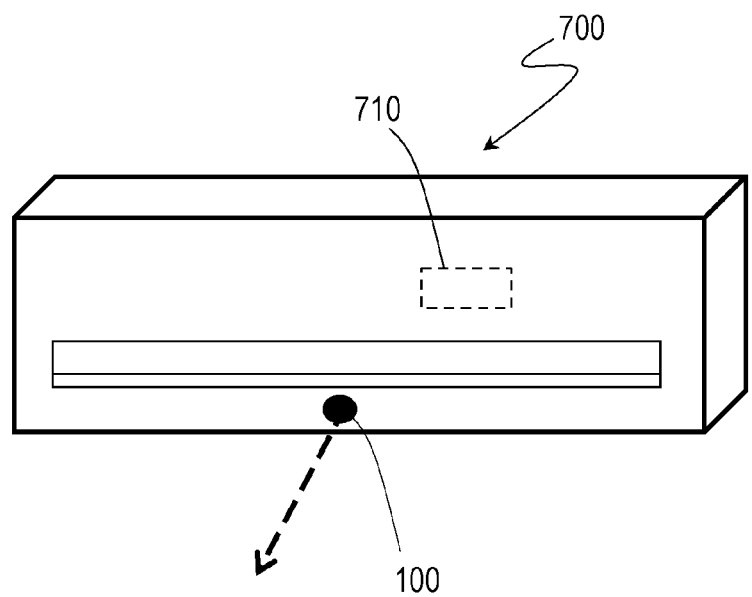
FIG. 19 schematically illustrates the external appearance of an environmental control device according to an eighth embodiment.

FIG. 19 schematically illustrates the external appearance of an environmental control device 700 according to an eighth embodiment.

The environmental control device 700 according to this embodiment includes the biological information detection device 100. The environmental control device 700 may be an air conditioner or an audio, for instance. A device capable of controlling such surrounding environment (such as temperature, sound, light, humidity and smell) of a user is referred to as an "environmental control device" in the present description. In this embodiment, the subject O may be one or a plurality of users of the environmental control device 700.

The environmental control device 700 irradiates the forehead of the subject O with infrared light, and estimates a mental state, specifically, the feeling or temperature sensation of the subject O using the NIRS.

The calculation circuit 200 of the biological information detection device 100 monitors the movement of the subject O, and identifies the subject O first. Subsequently, the calculation circuit 200 identifies the position of a test portion (for instance, forehead) of the subject O by image recognition. Based on the thus-identified position, the light source starts to irradiate the forehead with infrared light.

The environmental control device 700 includes a control circuit 710. The control circuit 710 generates a control signal of the environmental control device 700 based on the biological information from the calculation circuit 200 of the biological information detection device 100. Alternatively, the calculation circuit 200 may generate a control signal of the environmental control device 700 based on the biological information, and the control circuit 710 may control the environmental control device 700 based on the control signal. For instance, it is assumed that the biological information detection device 100 has detected discomfort of the subject O. In the case where the environmental control device 700 is an air conditioner, the environmental control device 700 can automatically turn on the power supply to start the operation or decrease or increase the preset temperature during the operation. In the case where the environmental control device 700 is an audio device, the environmental control device 700 may automatically turn the sound volume down, and may automatically select a music piece (such as a classical music piece) which is expected to provide a relaxing effect, for instance.

In the embodiments above, examples have been described in which near-infrared light and red light are mainly used as probes. However, the present disclosure is not limited to such examples. The technique in the present disclosure is also applicable to obtaining of information on the inside of a living body using electromagnetic waves with another wavelength, such as microwave.

What is claimed is:

1. A biological information detection device comprising:
a light source that, in operation, emits irradiation light for irradiating a test portion of a subject;
a light detector that, in operation, detects light reflected from the test portion and outputs an electrical signal corresponding to the light; and
a calculation circuit that, in operation, generates a signal of biological information related to a blood flow in a target area in the test portion based on the electrical signal, wherein
the light detector is an image sensor,
the electrical signal includes an image signal obtained by the image sensor, and
the calculation circuit, in operation, detects a magnitude of an inclination of an orientation of the test portion with respect to a reference orientation by image recognition based on the image signal, and determines the target area according to the magnitude of the inclination of the orientation of the test portion.

2. The biological information detection device according to claim 1, wherein, in operation, the calculation circuit determines at least one selected from the group consisting of a shape of the target area, and a position of the target area in the test portion.

3. The biological information detection device according to claim 1, wherein, in operation, the calculation circuit further determines whether or not the magnitude of the inclination of the orientation of the test portion has changed, and when it is determined that the magnitude of the inclination of the orientation of the test portion has changed, the calculation circuit changes a shape of the target area according to the magnitude of the inclination of the orientation of the test portion after the change.

4. The biological information detection device according to claim 1, wherein, in operation, the calculation circuit further determines whether or not the magnitude of the inclination of the orientation of the test portion has changed, and when it is determined that the magnitude of the inclination of the orientation of the test portion has changed, the calculation circuit changes a position of the target area in the test portion according to the magnitude of the inclination of the orientation of the test portion after the change.

5. The biological information detection device according to claim 1, wherein
the subject includes feature points, and
the calculation circuit, in operation,
extracts the feature points from the image signal, and
detects the magnitude of the inclination of the orientation of the test portion based on positions of the feature points in the image signal.

6. The biological information detection device according to claim 5, wherein
the calculation circuit, in operation,
predicts a propagation path of the light inside the test portion based on the magnitude of the inclination of the orientation of the test portion, and
determines the target area based on the predicted propagation path.

7. The biological information detection device according to claim 6, wherein
the calculation circuit, in operation,
predicts a intensity of the light emitted from the test portion or a rate of change of the intensity of the light with respect to a reference value based on at least one selected from the group consisting of the magnitude of the inclination of the orientation of the test portion and the predicted propagation path, and when the predicted intensity of the light or the predicted rate of change of the intensity of the light is smaller than a first value, increases an intensity of the signal of the biological information.

8. The biological information detection device according to claim 7, wherein when the predicted intensity of the light or the predicted rate of change of the intensity of the light is larger than a second value, the calculation circuit decreases the intensity of the signal of the biological information.

9. The biological information detection device according to claim 1, wherein
the light detector, in operation, outputs the electrical signal at a plurality of times, and
the calculation circuit, in operation, generates the signal of the biological information over time based on the electrical signal outputted from the light detector at the plurality of times.

10. The biological information detection device according to claim 1, wherein
the calculation circuit, in operation, further detects a distance between the test portion and the light detector based on the electrical signal, and
when the distance is longer than a predetermined distance, the calculation circuit increases an intensity of the signal of the biological information.

11. The biological information detection device according to claim 10, wherein when the distance is shorter than the predetermined distance, the calculation circuit decreases the intensity of the signal of the biological information.

12. The biological information detection device according to claim 10, wherein the calculation circuit, in operation, further determines whether or not the distance has changed, and when it is determined that the distance has changed, the calculation circuit changes the intensity of the signal the biological information to a value which is larger as the distance after the change is larger.

13. The biological information detection device according to claim 10, wherein for each of one or more pixels contained in an image signal which is in the image signal obtained by the image sensor and which corresponds to the test portion, the calculation circuit, in operation, detects the distance, generates the signal of the biological information, and adjusts the intensity of the signal of the biological information.

14. The biological information detection device according to claim 10, wherein the predetermined distance is the distance detected by the calculation circuit at a certain time.

15. The biological information detection device according to claim 10, wherein the predetermined distance is the distance detected by the calculation circuit when the generation of the signal of the biological information is started.

16. The biological information detection device according to claim 10, wherein
the irradiation light is pulsed light, and
the calculation circuit, in operation, detects the distance based on a time from when the light source emits the pulsed light to when the light detector detects the pulsed light.

17. The biological information detection device according to claim 10, further comprising:
a range sensor that detects a distance to the test portion,
wherein, in operation, the calculation circuit adjusts the intensity of the signal of the biological information based on the distance detected by the range sensor.

18. The biological information detection device according to claim 1, wherein the light contains a component with a wavelength of 650 nm or greater and 950 nm or less.

19. The biological information detection device according to claim 1, wherein
the test portion is a forehead of the subject, and
the biological information is information related to a blood flow in a cerebral cortex of the subject.

20. A biological information detection device comprising:
a calculation circuit that, in operation, generates a signal of biological information related to a blood flow in a target area in a test portion of a subject based on an image signal received from a device including a light source that, in operation, emits irradiation light for irradiating the test portion, and an image sensor that, in operation, detects light reflected from the test portion and outputs the image signal of the test portion,
wherein, in operation,
the calculation circuit detects a magnitude of an inclination of an orientation of the test portion with respect to a reference orientation by image recognition based on the image signal, and determines the target area according to the magnitude of the inclination of the orientation of the test portion.

* * * * *